(12) United States Patent
Grundmann et al.

(10) Patent No.: US 7,220,556 B1
(45) Date of Patent: May 22, 2007

(54) PREPARATION OF FACTOR XIIIA BY GENE MANIPULATION

(75) Inventors: Ulrich Grundmann, Marburg (DE); Egon Amann, Marburg (DE); Gerd Zettlmeissl, Lahntal (DE)

(73) Assignee: ZLB Behring GmbH, Marburg (DE)

( * ) Notice: Subject to any disclaimer, the term of this patent is extended or adjusted under 35 U.S.C. 154(b) by 0 days.

(21) Appl. No.: 08/459,044

(22) Filed: Jun. 2, 1995

Related U.S. Application Data

(63) Continuation of application No. 08/032,171, filed on Mar. 12, 1993, which is a continuation of application No. 07/549,234, filed on Jul. 9, 1990, now abandoned, which is a continuation of application No. 07/024,174, filed on Mar. 10, 1987, now abandoned.

(30) Foreign Application Priority Data

| Mar. 12, 1986 | (DE) | ............................. | P3608280 |
| Jun. 26, 1986 | (DE) | ............................. | P3621371 |

(51) Int. Cl.
| | | |
|---|---|---|
| *C12N 1/21* | (2006.01) | |
| *C12N 1/19* | (2006.01) | |
| *C12N 5/10* | (2006.01) | |
| *C12N 15/12* | (2006.01) | |
| *C12N 15/85* | (2006.01) | |

(52) U.S. Cl. .................. 435/69.1; 435/320.1; 435/325; 435/358; 435/252.3; 435/254.11; 435/254.21; 536/23.1; 536/23.2; 536/23.5

(58) Field of Classification Search ............... 435/69.1, 435/320.1, 325, 358, 252.3, 254.11, 254.21, 435/193, 240.2; 536/23.1, 23.2, 23.5; 530/381
See application file for complete search history.

(56) References Cited

U.S. PATENT DOCUMENTS

| 4,597,899 A | 7/1986 | Falke | ...................... 530/383 |
| 5,328,898 A | 7/1994 | Greenberg | ................... 514/12 |

FOREIGN PATENT DOCUMENTS

| EP | 0162426 | 11/1985 |
| EP | 0268772 | 6/1988 |
| GB | 2125409 | 3/1984 |

OTHER PUBLICATIONS

Bowie et al. Science 247:1306–1310, 1990.*
Wells. Biochemistry 29:8509–8517, 1990.*
Ngo et al. The Protein Folding Problem and Tertiary Structure Prediction, Merz et al., eds., Birkhauser, boston, pp. 491–496, 1994.*
M. Schwartz et al., J. Biol. Chem., vol. 248, No. 4, pp. 1395–1407 (1973).
J. Millan, J. Biol. Chem., vol. 261, No. 7, pp. 3112–3115 (1986).
U. Grundmann et al., Proc. Natl. Acad. Sci. USA, vol. 83, pp. 8024–8028 (1986).
A. Ichinose et al., Biochemistry, vol. 25, No. 22, pp. 6900–6906 (1986).
P.G. Board et al., Human Genetics, vol. 67, pp. 406–408 (1984).
H. Lorand et al., Methods in Enzymology, vol. 80, pp. 333–341 (1981).
N. Takahashi et al., Primary Structure of Blood Coagulation Factor XIII a (firbrinoligase, transglutaminase) from Human Placenta, Proc. Natl. Acad. Sci. USA, vol. 83, pp. 8019–8023, (1986).

* cited by examiner

*Primary Examiner*—Elizabeth C. Kemmerer
(74) *Attorney, Agent, or Firm*—Len S. Smith; Reza Green; Richard Bork

(57) ABSTRACT

The cDNA which codes for factor XIIIa has been isolated using a cDNA bank from human placenta and probes constructed on the basis of the amino acid sequence of factor XIIIa peptide fragments. It is possible with this cDNA not only to obtain factor XIIIa by gene manipulation in high purity but also to prepare diagnostic aids which permit the analysis of genetic factor XIIIa defects. Furthermore, it is possible on the basis of the amino acid sequence to prepare antibodies which are suitable for diagnostic aids and antibody columns.

37 Claims, 16 Drawing Sheets

1
GAGGAAGTCCCCGAGGCGCACAGAGCAAGCCCCACGCGAGGGCACCTCTGGAGGGGAGCGCCTGCAGGACCTTGTAAAGTC

81
AAAA MET SER GLU THR SER ARG THR ALA PHE GLY GLY ARG ARG ALA VAL PRO PRO ASN ASN
     ATG TCA GAA ACT TCC AGG ACC GCC TTT GGA GGC AGA AGA GCA GTT CCA CCC AAT AAC

142
SER ASN ALA ALA GLU ASP ASP LEU PRO THR VAL GLU LEU GLN GLY VAL VAL PRO ARG GLY
TCT AAT GCA GCG GAA GAT GAC CTG CCC ACA GTG GAG CTT CAG GGC GTG GTG CCC CGG GGC

202
VAL ASN LEU GLN GLU PHE LEU ASN VAL THR SER VAL HIS LEU PHE LYS GLU ARG TRP ASP
GTC AAC CTG CAA GAG TTT CTT AAT GTC ACG AGC GTT CAC CTG TTC AAG GAG AGA TGG GAC

262
THR ASN LYS VAL ASP HIS HIS THR ASP LYS TYR GLU ASN ASN LYS LEU ILE VAL ARG ARG
ACT AAC AAG GTG GAC CAC CAC ACT GAC AAG TAT GAA AAC AAC AAG CTG ATT GTC CGC AGA

322
GYL GLN SER PHE TYR VAL GLN ILE ASP LEU SER ARG PRO TYR ASP PRO ARG ARG ASP LEU
GGG CAG TCT TTC TAT GTG CAG ATT GAC CTC AGT CGT CCA TAT GAC CCC AGA AGG GAT CTC

FIG. 6-1

382
PHE ARG VAL GLU TYR VAL ILE GLY ARG TYR PRO GLN GLU ASN LYS GLY THR TYR ILE PRO
TTC AGG GTG GAA TAC GTC ATT GGT CGC TAC CCA CAG GAG AAC AAG GGA ACC TAC ATC CCA

442
VAL PRO ILE VAL SER GLU LEU GLN SER GLY LYS TRP GLY ALA LYS ILE VAL MET ARG GLU
GTG CCT ATA GTC TCA GAG TTA CAA AGT GGA AAG TGG GGG GCC AAG ATT GTC ATG AGA GAG

502
ASP ARG SER VAL ARG LEU SER ILE GLN SER SER PRO LYS CYS ILE VAL GLY LYS PHE ARG
GAC AGG TCT GTG CGG CTG TCC ATC CAG TCT TCC CCC AAA TGT ATT GTG GGG AAA TTC CGC

562
MET TYR VAL ALA VAL TRP THR PRO TYR GLY VAL LEU ARG THR SER ARG ASN PRO GLU THR
ATG TAT GTT GCT GTC TGG ACT CCC TAT GGC GTA CTT CGA ACC AGT CGA AAC CCA GAA ACA

622
ASP THR TYR ILE LEU PHE ASN PRO TRP CYS GLU ASP ASP ALA VAL TYR LEU ASP ASN GLU
GAC ACG TAC ATT CTC TTC AAT CCT TGG TGT GAA GAT GAT GCT GTG TAT CTG GAC AAT GAG

682
LYS GLU ARG GLU GLU TYR VAL LEU ASN ASP ILE GLY VAL ILE PHE TYR GLY GLU VAL ASN
AAA GAA AGA GAA GAG TAT GTC CTG AAT GAC ATC GGG GTA ATT TTT TAT GGA GAG GTC AAT

FIG. 6-2

```
742
ASP ILE LYS THR ARG SER TRP SER TYR GLY GLN PHE GLU ASP GLY ILE LEU ASP THR CYS
GAC ATC AAG ACC AGA AGC TGG AGC TAT GGT CAG TTT GAA GAT GGC ATC CTG GAC ACT TGC

802
LEU TYR VAL MET ASP ARG ALA GLN MET ASP LEU SER GLY ARG GLY ASN PRO ILE LYS VAL
CTG TAT GTG ATG GAC AGA GCA CAA ATG GAC CTC TCT GGA AGA GGG AAT CCC ATC AAA GTC
                                    |__66 mer__|

862
SER ARG VAL GYL SER ALA MET VAL ASN ALA LYS ASP ASP GLU GLY VAL LEU VAL GLY SER
AGC CGT GTG GGG TCT GCA ATG GTG AAT GCC AAA GAT GAC GAA GGT GTC CTC GTT GGA TCC

922
TRP ASP ASN ILE TYR ALA TYR GLY VAL PRO PRO SER ALA TRP THR GLY SER VAL ASP ILE
TGG GAC AAT ATC TAT GCC TAT GGC GTC CCC CCA TCG GCC TGG ACT GGA AGC GTT GAC ATT

982
LEU LEU GLU TYR ARG SER SER GLU ASN PRO VAL ARG TYR GLY GLN CYS TRP VAL PHE ALA
CTA TTG GAA TAC CGG AGC TCT GAG AAT CCA GTC CGG TAT GGC CAA TGC TGG GTT TTT GCT

1042
GLY VAL PHE ASN THR PHE LEU ARG CYS LEU GLY ILE PRO ALA ARG ILE VAL THR ASN TYR
GGT GTC TTT AAC ACA TTT TTA CGA TGC CTT GGA ATA CCA GCA AGA ATT GTT ACC AAT TAT
```

FIG. 6-3

```
1102
PHE SER ALA HIS ASP ASN ASP ALA ASN LEU GLN MET ASP ILE PHE LEU GLU GLU ASP GLY
TTC TCT GCC CAT GAT AAT GAT GCC AAT TTG CAA ATG GAC ATC TTC CTG GAA GAA GAT GGG

1162
ASN VAL ASN SER LYS LEU THR LYS ASP SER VAL TRP ASN TYR HIS CYS TRP ASN GLU ALA
AAC GTG AAT TCC AAA CTC ACC AAG GAT TCA GTG TGG AAC TAC CAC TGC TGG AAT GAA GCA

1222
TRP MET THR ARG PRO ASP LEU PRO VAL GLY PHE GLY GLY TRP GLN ALA VAL ASP SER THR
TGG ATG ACA AGG CCT GAC CTT GTT GGA TTT GGA GGC TGG CAA GCT GTG GAC AGC ACC

1282
PRO GLN GLU ASN SER ASP GLY MET TYR ARG CYS GLY PRO ALA SER VAL GLN ALA ILE LYS
CCC CAG GAA AAT AGC GAT GGC ATG TAT CGG TGT GGC GCC TCG GTT CAA GCC ATC AAG

1342
HIS GLY HIS VAL CYS PHE GLN PHE ASP ALA PRO PHE VAL PHE ALA GLU VAL ASN SER ASP
CAC GGC CAT GTC TGC TTC CAA TTT GAT GCA CCT TTT GTT TTT GCA GAG GTC AAC AGC GAC

1402
LEU ILE TYR ILE THR ALA LYS LYS ASP GLY THR HIS VAL VAL GLU ASN VAL ASP ALA THR
CTC ATT TAC ATT ACA GCT AAG AAA GAT GGC ACT CAT GTG GTG GAA AAT GTG GAT GCC ACC
```

FIG. 6-4

1462
HIS ILE GLY LYS LEU ILE VAL THR LYS GLN ILE GLY GLY ASP GLY MET MET ASP ILE THR
CAC ATT GGG AAA TTA ATT GTG ACC AAA CAA ATT GGA GGA GAT GGC ATG ATG GAT ATT ACT 20 mer 1522
ASP THR TYR LYS PHE GLN GLU GLY GLN GLU GLU ARG LEU ALA LEU GLU THR ALA LEU
GAT ACT TAC AAA TTC CAA GAA GGT CAA GAA GAG AGA TTG GCC CTA GAA ACT GCC CTG 1582
MET TYR GLY ALA LYS LYS PRO LEU ASN THR GLU GLY VAL MET LYS SER ARG SER ASN VAL
ATG TAC GGA GCT AAA AAG CCC CTC AAC ACA GAA GGT GTC ATG AAA TCA AGG TCC AAC GTT 1642
ASP MET ASP PHE GLU VAL GLU ASN ALA VAL LEU GLY LYS ASP PHE LYS LEU SER ILE THR
GAC ATG GAC TTT GAA GTG GAA AAT GCT GTG CTG GGA AAA GAC TTC AAG CTC TCC ATC ACC 1702
PHE ARG ASN ASN SER HIS ASN ARG TYR THR ALA TYR LEU SER ALA ASN ILE THR
TTC CGG AAC AAC AGC CAC AAC CGT TAC ACC ATC ACA GCT TAT CTC TCA GCC AAC ATC ACC 1762
PHE TYR THR GLY VAL PRO LYS ALA GLU PHE LYS LYS GLU THR PHE ASP VAL THR LEU GLU
TTC TAC ACC GGG GTC CCG AAG GCA GAG TTC AAG AAG GAG ACG TTC GAC GTG ACG CTG GAG

FIG. 6-5

```
1822
PRO LEU SER PHE LYS LYS GLU ALA VAL LEU ILE GLN ALA GLY GLU TYR MET GLY GLN LEU
CCC TTG TCC TTC AAG AAA GAG GCG GTG CTG ATC CAA GCC GGC GAG TAC ATG GGT CAG CTG

1882
LEU GLU GLN ALA SER LEU HIS PHE PHE VAL THR ALA ARG ILE ASN GLU THR ARG ASP VAL
CTG GAA CAA GCG TCC CTG CAC TTC TTT GTC ACA GCT CGC AAT GAG ACC AGG GAT GTT

1942
LEU ALA LYS GLN LYS SER THR VAL LEU THR ILE PRO GLU ILE ILE LYS VAL ARG GLY
CTG GCC AAG CAA AAG TCC ACC GTG CTA ACC ATC CCT GAG ATC ATC AAG GTC CGT GGC

2002
THR GLN VAL VAL GLY SER ASP MET THR VAL GLN PHE THR ASN PRO LEU LYS GLU
ACT CAG GTT GTT GGT TCT GAC ATG ACT GTG CAG TTT ACC AAT CCT TTA AAA GAA

2062
THR LEU ARG ASN VAL TRP VAL HIS LEU ASP GLY PRO GLY VAL THR ARG PRO MET LYS LYS
ACC CTG CGA AAT GTC TGG GTA CAC CTG GAT GGT CCT GGA GTA ACA AGA CCA ATG AAG AAG

2122
MET PHE ARG GLU ILE ARG PRO ASN SER THR VAL GLN TRP GLU GLU VAL CYS ARG PRO TRP
ATG TTC CGT GAA ATC CGG CCC AAC TCC ACC GTG CAG TGG GAA GAA GTG TGC CGG CCC TGG
```

FIG. 6-6

2182
VAL SER GLY HIS ARG LYS LEU ILE ALA SER MET SER SER ASP SER LEU ARG HIS VAL TYR
GTC TCT GGG CAT CGG AAG CTG ATA GCC AGC ATG AGC AGT GAC TCC CTG AGA CAT GTG TAT

2242
GLY GLU LEU ASP VAL GLN ILE GLN ARG ARG PRO SER MET $$$ ATGCACAGGAAGCTGAGATGAAC
GGC GAG CTG GAC GTG CAG ATT CAA AGA CGA CCT TCC ATG TGA

2307
CCTGGCATTTGGCCTCTCTTGTAGTCTTGGCTAAGGAAATTCTAACGCAAAAATAGCTCTTGCTTTGACTTAGGTGTGAAGA

2387
CCCAGACAGGACTGCAGAGGGCCCCAGAGTGGAGATCCCACATATTCAAAAACATACTTTTCCAAACCCAGGCTATTCG

2467
GCAAGGAAGTTAGTTTTTAATCTCTCCACCTTCCAAAGAGTGCTAAGCATTAGCTTTAATTAAGCTCTCATAGCTCATAA

2547
GAGTAACAGTCATCATTATCATCACAAATGGCTACATCTCCAAATATCAGTGGCTCTCTTACCAGGGAGATTTGCTCA

2627
ATACCTGGCCTCATTTAAAACAAGACTTCAGATTCCCCACTCAGCCTTTTGGGAATAATAGCACATGATTTGGGCTCTAG

FIG. 6-7

2707 AATTCCAGTCCCCTTTCTCGGGTCAGTTCTACCCTCCATGTGAGAATATTTTCCCAGGACTAGAGCACAACATAATT

2787 TTTATTTTTGGCAAAGCCAGAAAAAGATCTTTCATTTTGCACCTGCAGCCAAGCAAATGCCTGCCAAATTTTAGATTTAC

2867 CTTGTTAGAAGAGGTGGCCCCATATTAACAAATTGCATTTGTGGGAAACTTAACCACCTACAAGGAGATAAGAAAGCAGG

2947 TGCAACACTCAAGTCTATTGAATAATGTAGTTTTGTGATGCATTTTATAGAATGTGTCACACTGTGGCCTGATCAGCAGG

3027 AGCCAATATCCCTTACTTTAACCCTTTCTGGGATGCAATACTAGGAAGTAAAGTGAAGAATTTATCTCTTTAGTTAGTGA

3107 TTTATATTTCACCATCTCTCAGGAATCATCTCCTTTGCAGAATGATGCAGGTTCAGGTCCCCTTTCAGAGATATAATAAG

3187 CCCAACAAGTTGAAGAAGCTGGCGGATCTAGTGACCAGATATATAGAAGGACTGCAGCCACTGATTCTCTCTTGTCCTTC

3267 ACATCACCATTTTGAGACCTCAGCTTGGCACTCAGGTGCTGAAGGGTAATATGGACTCAGCCTTGCAAATAGCCAGTGCT

FIG. 6-8

```
3347
AGTTCTGACCCAACCACAGAGGATGCTGACATCATTTGTATTATGTTCCAAGGCTACTACAGAGAAGGCTGCCTGCTATG

3427
TATTTGCAAGGCTGATTTATGTTCAGAATTTCCCTCTGATATGTCTTAGGGTGTGATTTAGGTCAGTAGACTGTGATTCTT

3507
AGCAAAAAATGAACAGTGATAAGTATACTGGGGGCAAAATCAGAATGCTCTGGTCTATATATAACCACATTTCTGAG

3587
CCTTTGAGACTGTTCCTGAGCCCTTCAGCACTAACCTATGAGGGTGAGCTGGTCCCCTCTATATATACATCATACTTAACT

3667
TTACTAAGTAATCTCACAGCATTTGCCAAGTCTCCCAATATCCAATTTTAAAATGAAATGCATTTTGCTAGACAGTTAAA

3747
CTGGCTTAACTTAGTATATATTATTATTAATTACAATGTAATAGAAGCTTAAATAAGTTAAACTGATTATAAAAAAAAA

3827
AAAAAAAAAAAAAAAAAAAAAAAAAAAAAAAAAAAAAAAAAAAAAAAAAAAAAAAAAAAAAAAAAAAAAAAAAAAAAAA
```

FIG. 6-9

PREPARATION OF FACTOR XIIIA BY GENE MANIPULATION

This is a continuation of application Ser. No. 08/032,171, filed Mar. 12, 1993, which is a continuation application of Ser. No. 07/549,234, filed Jul. 9, 1990, abandoned, which is a continuation application of Ser. No. 07/024,174 filed Mar. 10, 1987, abandoned.

Coagulation factor XIII is the final member of the "coagulation cascade" in the natural process of blood coagulation in vertebrates. The enzymatically active form of factor XIII, factor XIIIa, also called "activated fibrin-stabilizing factor", "fibrinoligase" or "plasma transglutaminase" and, hereinafter, "F XIIIa", catalyzes the fusion of fibrin units in preexistent thrombi by intramolecular crosslinking (Lorand et al., Methods in Enzymology 80 (1981), 333–341; Curtis et al., Annals New York Academy of Sciences 1983, 567–576). The molecular weight of factor XIII from plasma is about 300 kD (Loewy et al., J. Biol. Chem. 236 (1961) 2634). The molecular weight of the active subunit F XIIIa is about 80 kD (Bohn and Schwick, Arzneimittelforschung 21 (1971) 1432). During the activation of factor XIII, thrombin splits off from the precursor a peptide which is about 4 kD in size and has a known sequence of 36 amino acids (Takagi and Doolittle, Biochemistry 13 (1974) 750–756). In addition, a sequence embracing four amino acids is known (Holbrook et al., Biochem. J. 135 (1973) 901–903).

The invention relates to a process for the preparation of F XIIIa by gene manipulation, to the mRNA necessary for this, to the cDNA obtained therefrom, to DNA structures and vectors containing all or part of this cDNA, to cells transformed with DNA of this type, and to the polypeptide expressed by these cells. The invention also relates to part-sequences of the amino acid sequence of F XIIIa, to specific antibodies obtained therewith, to diagnostic aids and antibody columns produced from these antibodies, and to a polypeptide obtained with the aid of such columns. Another aspect of the invention relates to diagnostic aids which contain all or part of the DNA or RNA coding for F XIIIa, and to diagnostic methods with which body fluids and tissues are examined using diagnostic aids of this type. Further aspects of the invention and its preferred embodiments are illustrated in detail hereinafter and defined in the patent claims.

The drawings, in which the numbers coincide with those in the examples, illustrate the invention:

FIG. 6 discloses the amino acid sequence of Factor XIIIa.

The amino acid sequence of F XIIIa fragments was determined for the construction of suitable probes. The corresponding peptide fragments were obtained by proteolysis or cleavage with cyanogen bromide. Based on knowledge of the amino acid sequences of such fragments, two oligonucleotide probes were synthesized, one 20mer and one 66mer.

In the 20mer probe all theoretically possible codons for the amino acid sequence Met-Met-Asp-Ile-Thr-Asp-Thr were taken into account, with, in the case of the last amino acid, the third position in the codon being omitted. The 20mer probe is thus 48-fold degenerate, i.e. a mixture of all 48 theoretically possible oligonucleotides coding for the said amino acid sequence (Table 1; Appendix).

The 66mer probe was selected on the basis of the following amino acid sequence

Tyr-Gly-Gln-Phe-Glu-Asp-Gly-Ile-Leu-Asp-Thr-Cys-Leu-Tyr-Val-Met-Asp-Arg-Ala-Gln-Met-Asp and with the assistance of statistical data (Lathe, J. Molec. Biol. 183 (1985) 1–12) (Table 2, Appendix).

Figure 1:
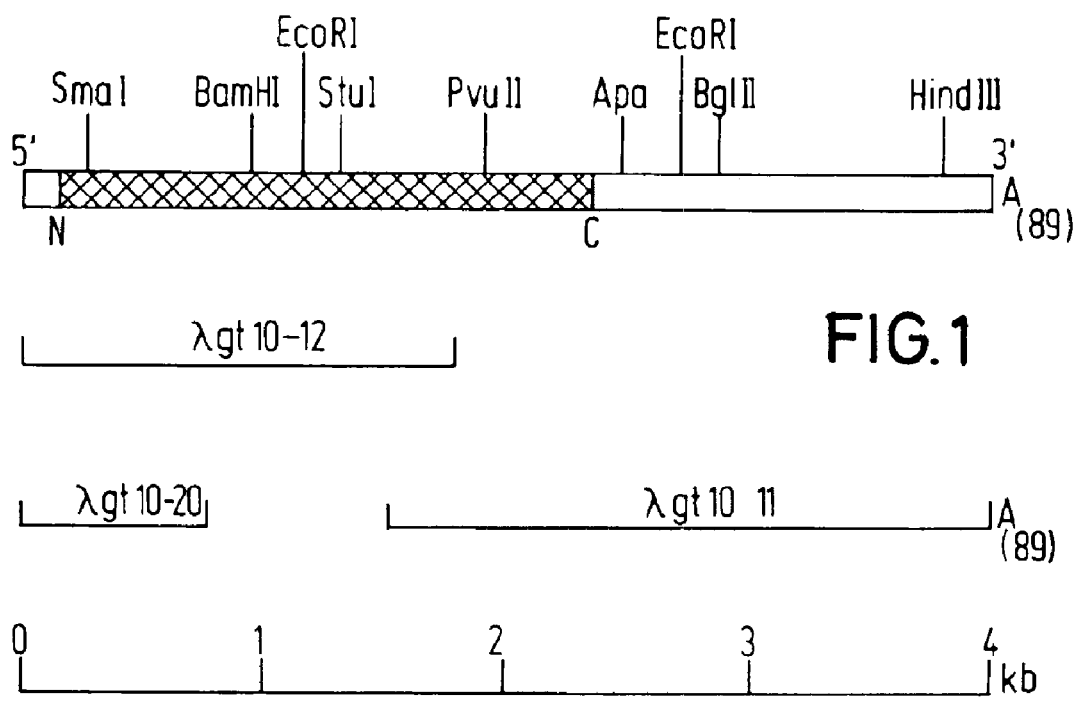
FIG. 1 shows the cDNA coding for F XIIIa (the coding region being shaded) and, below this, the DNA regions of the isolated and characterized clones.

These probes were used to screen a cDNA bank. The cDNA was prepared from mRNA from a mature human placenta, the mRNA being isolated from the latter, and the cDNA being prepared therefrom. The cDNA was provided with EcoRI ends and ligated into the EcoRI cleavage site of the phage vector λgt10. A positive clone, λgt10-12, which was identified with the abovementioned probe, was further analyzed (FIG. 1). The sequencing, by methods known per se, resulted in the DNA sequence which codes for F XIIIa.

Rescreening of the cDNA bank with this DNA sequence resulted in isolation of further clones which expand both towards the 5'- and towards the 3'-end.

FIG. 1 shows the restriction map of the DNA sequence which codes for F XIIIa. "N" designates the N-terminal end and "C" designates the C-terminal end of the coding region, and "$A_{(89)}$" designates the poly(A) sequence of 89 bases. This sequence represents the whole of the coding sequence of F XIIIa. Table 3 (Appendix) shows the DNA sequence found (coding strand) and, deduced therefrom, the amino acid sequence from the cloned cDNA fragments from λgt10-11 and λgt10-12. The total length of the cDNA is 3905 base-pairs. The N-terminal sequence embracing 36 amino acids found by Takagi and Doolittle (loc. cit.) is present in the sequence which was found. This sequence is indicated in Table 3 with an unbroken line between nucleotide positions 88 and 198. In addition to the sequence found by Takagi and Doolittle, the cDNA codes for a valine in nucleotide positions 187–189. The sequence embracing four amino acids found by Holbrook et al. (loc. cit.)—Gly-Gln-Cys-Trp—is coded for by the cDNA in positions 1021–1032. This sequence is likewise indicated by an unbroken line. In addition, the positions of the 20mer and 66mer oligonucleotide probes are indicated by broken lines. The 20mer probe hybridizes between positions 1507 and 1526, and the 66mer probe hybridizes between positions 766 and 831.

It is possible according to the invention to use the coding cDNA for the preparation of modified genes which code for proteins having altered biological properties. It is possible for this purpose to undertake, in a manner known per se, deletions, insertions and base-exchanges.

It is also possible, by the choice of the host, to influence the nature of the modification to the F XIIIa. Thus, there is no glycosylation in bacteria, while that taking place in yeast cells differs from that in higher eukaryotic cells.

Knowing the amino acid sequence of F XIIIa, it is possible to prepare, by conventional methods or gene manipulation, part-sequences of amino acids which can act as antigens for the preparation of polyclonal or monoclonal antibodies. Such antibodies can be used not only for diagnostic purposes but also for the preparation of antibody columns with which it is possible to remove F XIIIa from solutions which contain this factor in addition to other proteins.

It is also possible, by use of the cDNA or parts thereof, straightforwardly to isolate from a genomic bank the genomic clone which codes for F XIIIa and using which it is possible not only to express it in eukaryotic cells but also to gain further diagnostic information.

F XIIIa deficiencies can result in various syndromes which, to a large extent, are attributed to the inability to convert the precursors into the active form of the enzyme. Knowledge of the cDNA of F XIIIa now permits the preparation of diagnostic aids with which it is possible straightforwardly to establish whether genetic modifications are present.

Thus, it is possible according to the invention to prepare a highly pure factor XIIIa without any risk of contamination by, for example, viruses or other proteins. The dependence, which has existed to date, on human plasma or placentae as source of raw material has thus been overcome. In addition, the invention allows access to valuable diagnostic aids and thus the analysis of genetic F XIIIa defects.

The invention is illustrated in detail in the examples which follows. Unless otherwise stated, percentages relate to weight where they do not relate to amounts.

Apart from those explained in the text, the following abbreviations have been used:

| EDTA = | sodium ethylenediaminetetraacetate |
|---|---|
| SDS = | sodium dodecyl sulfate |
| DTT = | dithiothreitol |
| BSA = | bovine serum albumin |

EXAMPLES

1. Isolation of RNA from human placenta

RNA was obtained from a mature human placenta (by the method of Chirgwin et al., Biochemistry 18 (1979) 5294–5299). About 10 g of placental tissue was ground in liquid nitrogen, suspended in 80 ml of 4 M guanidinium thiocyanate containing 0.1 M mercaptoethanol and treated in a homogenizer (Ultraturrax) at 20,000 rpm for 90 sec. The lysate was centrifuged at 7,000 rpm for 15 min. (Sorvall GSA rotor) and 2 ml of 1 M acetic acid and 60 ml of abs. ethanol were added to the supernatant, which was allowed to precipitate at −20° C. overnight. After sedimentation at 6,000 rpm and −10° C. for 10 min, the nucleic acids were completely dissolved in 40 ml of 7.5 M guanidinium hydrochloride (pH 7.0) and precipitated with a mixture of 1 ml of 1 M acetic acid and 20 ml of abs. ethanol. To remove the DNA the precipitation was repeated once more with half the volumes. The RNA was dissolved in 12 ml of $H_2O$, precipitated with a mixture of 1.2 ml of 4 M potassium acetate and 24 ml of abs. ethanol, sedimented and finally redissolved in 10 ml of $H_2O$ (1 ml per g tissue).

Isolation of placental mRNA containing poly(A)

To isolate mRNA containing poly(A), the placental RNA was fractionated by oligo(dT)-cellulose chromatography (Aviv and Leder, Proc. Natl. Acad. Sci. USA 69 (1973) 1408–1412) in 2 ml Pasteur pipettes in LiCl. About 5 mg of placental RNA were applied to the column in buffer 1 (500 mM LiCl, 20 mM tris (pH 7.5), 1 mM EDTA, 0.1% SDS). Whereas the poly(A)$^+$ RNA was bound to the oligo(dT)-cellulose, the poly(A)$^−$ RNA could be eluted again. After a wash with buffer 2 (100 mM LiCl, 29 mM tris (pH 7.5), 1 mM EDTA, 0.1% SDS), the poly(A)$^+$ RNA (placental mRNA) was eluted from the column with buffer 3 (5 mM tris (pH 7.5), 1 mM EDTA, 0.05% SDS).

For further purification, the poly(A)$^+$ RNA was adjusted to buffer 1 and rechromatographed on oligo(dT)-cellulose. After this second purification step, the yield of placental poly(A)$^+$ RNA was about 4% of the RNA used.

Synthesis of cDNA from human placenta (placental cDNA) and double-stranded cDNA (dsDNA)

Before the cDNA synthesis, a check that the placental mRNA containing poly(A) was intact was carried out in a 1.5% agarose gel.

Then 4 µg of placental mRNA were dissolved in 65.5 µl of $H_2O$, denatured at 70° C. for 10 min, and cooled again in ice. The cDNA was synthesized in a 100 µl mixture after addition of 20 µl of $RT_1$ buffer (250 mM tris (pH 8.2) at 42° C., 250 mM KCl, 30 mM $MgCl_2$), 2.5 µl of 20 mM dNTP (i.e. all four deoxynucleoside triphosphates), 1 µl of 1 µg/ml oligo(dT), 1 µl of 1 M DTT, 2 µl of RNAsin and 8 µl of reverse transcriptase (24 U/µl) at 42° C. for 90 min.

Double-stranded cDNA (dsDNA) was synthesized by the method of Gubler and Hoffmann (Gene 25 (1983) 263–269). The synthesis was carried out immediately after the cDNA synthesis by addition of 305.5 µl of $H_2O$, 80 µl of $RT_2$ buffer (100 mM tris (pH 7.5), 25 mM $MgCl_2$, 500 mM KCl, 50 mM DTT, 250 µg/ml BSA), 2 µl of RNase H (2 U/µl), 2.5 µl of E. coli DNA ligase (5 U/µl), 5 µl of 15 mM β-NAD, and 5 µl of DNA polymerase 1 (5 U/µl) and incubation at 15°0 C. for 5 h. The reaction was stopped by heat inactivation (70° C., 30 min).

After addition of 55 µl of 250 µM dNTP, 55 µl of 10 mM tris (pH 7.5), 10 mM $MgCl_2$, 10 µg/ml BSA, 3 µl of T4 DNA polymerase 1 (1 U/µl), 2 µl RNase H (2 U/µl) and 2 µl of RNase A (2 µg/ml), the reaction mixture was incubated at 37° C. for a further 30 min in order to correct faulty syntheses of the polymerase I on the second DNA strand ("repair reaction").

Ligation of EcoRI linkers to the dsDNA, and opening of the linkers

To set up a placental cDNA bank, the dsDNA was provided with EcoRI ends in order to be able to ligate it in the EcoRI cleavage site of the phage vector λgt10 (T. Maniatis et al. (1982), Molecular Cloning, A Laboratory Manual, Cold Spring Harbor). For this purpose of the dsDNA was a) treated with EcoRI methylase in order to protect internal EcoRI cleavage sites of the dsDNA, and b) provided with EcoRI linkers which c) were then opened with EcoRI.

Re a):

The methylase reaction of the dsDNA was carried out immediately after the repair reaction by addition of 25 µl of 500 mM EDTA (pH 8.0), 60 µl of methylase buffer (100 mM NaOAc (pH 5.2), 2 mg of S-adenosyl-L-methionine) and 2 µl of EcoRI methylase (20 U/µl) by incubation at 37° C. for 30 min.

The reaction mixture was extracted with phenol, and the dsDNA was precipitated with 60 µl of 4 M NaOAc and 1300 µl of ethanol. The dsDNA was washed twice with 70% ethanol, extracted once by shaking with ether, and dried.

Re b):

The EcoRI-methylated dsDNA was dissolved in 88 µl of $H_2O$ and, after addition of 10 µl of ligase buffer (500 mM tris (pH 7.4), 100 mM $MgCl_2$, 100 mM DTT, 10 mM spermidine, 10 mM ATP, 1 mg/ml BSA) and 1 µl of T4 DNA ligase (10 U/µl), was ligated with 1 µl of EcoRI linkers (0.5 µg/µl) (pGGAATTCC and pAGAATTCT) at 15° C. overnight.

Re c):

The volume of the ligase mixture was made up to 120 µl with 6 µl of H$_2$O, 12 µl of 10× EcoRI buffer and 2 µl of EcoRI (120 U/µl). The EcoRI digestion was carried out at 37° C. for 2 h.

Removal of unbound linkers via a potassium acetate gradient and size-selection of the dsDNA To remove all the unbound EcoRI linkers from the dsDNA, the EcoRI reaction mixture was applied in toto to a potassium acetate gradient (5–20% KOAc, 1 mM EDTA, 1 µl/ml ethidium bromide) which was centrifuged (Beckman SW 65/rotor) at 50,000 rpm and 20° C. for 3 h. The gradient was fractionated from below in such a way that the volume of the first five fractions was 500 µl, and that of all the remainder was 100 µl. The fractions were precipitated with 0.01 volume of acrylamide (2 mg/ml) and 2.5 volumes of ethanol, washed once with 70% strength ethanol and dried, and each was taken up in 5 µl of H$_2$O.

To determine the size of the dsDNA, 1 µl of each fraction was analyzed in a 1.5% agarose gel. In addition, the quantity of dsDNA was determined on 1 µl of each fraction.

Fractions containing dsDNA with over 1000 bp were combined, and the sample was concentrated until the final concentration was 27 µg/ml.

Incorporation of the dsDNA into the phage vector λgt10 and in vitro packaging reaction The incorporation of the dsDNA into the EcoRI cleavage site of the phage vector λgt10 (Vector Cloning Systems, San Diego, Calif.) was carried out in a 4 µl ligase mixture: 2 µl of dsDNA, 1 µl of λgt10 × EcoRI (1 µg/ml), 0.4 µl of ligase buffer, 0.5 µl of H$_2$O and 0.1 µl of T4 DNA ligase. The mixture was incubated at 15° C. for 4 h.

To establish the placental cDNA bank in the phase vector λgt10, the ligase mixture was then subjected to an in vitro packaging reaction with the λ-lysogenic cell extracts E. coli NS 428 and NS 433 at room temperature for 2 h (Vector Cloning Systems, San Diego, Calif.; Enquist and Sternberg, Methods in Enzymology 68, (1979), 281–298). The reaction was stopped with 500 µl of suspensions medium (SM: 0.1 M NaCl, 8 mM MgSO$_4$, 50 mM tris (pH 7.5), 0.01% gelatine) and 2 drops of chloroform.

Determination of the titer and analysis of the placental cDNA bank

The number of plaque-forming units (PFU) of the placental cDNA bank was determined using competent cells of the E. coli K 12 strain C600 HFL: it was 1×10$^6$ PFU. About 80% of the phages contained DNA inserts larger than 1000 base-pairs.

Oligonucleotide probes for screening the placental cDNA bank

Two oligonucleotide probes (20mer probe and 66mer probe) were synthesized for analysis of the placental cDNA bank. Their sequences were deduced from the amino acid primary sequence of several proteolytic and BrCN fragments of F XIIIa. In some cases overlapping, and hence longer, amino acid sequences were found, and these permitted the synthesis of a very long probe, namely the 66mer probe.

The 20mer probe is a conventional DNA probe in which all the theoretically possible codons for the amino acid sequence Met-Met-Asp-Ile-Thr-Asp-Thr are taken into account (in the case of the terminal amino acid, Thr, the third position in the codon, called the "wobble" position, was omitted; see Table 1). The 20mer probe is thus 48-fold degenerate, i.e. a mixture of all the 48 theoretically possible coding oligonucleotides for the said amino acid sequence.

The manner of construction and the use of the 66mer probe essentially followed the rules of Lathe, J. Mol. Biol. 183 (1985) 1–12. In order to construct the 66mer probe two 39mer probes were synthesized (39mer A with the sequence: 5' TATGGCCAGTTTGAGGATGGCATCCTG-GACACCTGTCTG 3'; and 39mer B with the sequence: 5' GTCCATCTGGGCCCGGTCCATCACATA-CAGACAGGTGTC 3'). 39mer A and 39mer B have a complementary sequence comprising 12 bases so that hybridization of the two sequences results in long free 5' ends.

The two 39mer probes were (as was the 20mer probe) labeled at the 5' end with T4 polynucleotide kinase in the presence of (γ-$^{32}$P)-ATP (about 1 µg of DNA, (γ-$^{32}$P)-ATP: 3000 Ci/mmol, 10 µCi/µl, with 6 µl/40 µl reaction mixture being used). The 20mer probe had a specific activity of 1×10$^8$ Bq/µg or 1.5×10$^6$ Bq/pmol. The two 39mer probes were heated at 95° C. for 5 min., mixed and slowly cooled to 4° C. in a cold room, and thus hybridized. Then about 1 µg of the hybridized 39mer probes was treated with DNA polymerase I, Klenow fragment, with the addition of (α-$^{32}$P)-dATP (3000 Ci/mmol, 10 µCi/µl, 4 µl/50 µl reaction mixture) (5'→3' filling-in reaction). The filled-in 66mer probe had a specific activity of 1.5×10$^8$ Bq/µg. The DNA probes were stored at −20° C.; the 20mer probe was used immediately for analysis (screening), while the 66mer probe had previously been heated at 95° C. for 5 min and then rapidly cooled in an ice bath.

Since the 66mer probe had been produced by hybridization of two 39mers followed by a 5'→3' filling-in reaction, it is possible to carry out various experiments. On the one hand, it is possible to hybridize cDNA banks with the denatured 66mer DNA probe and, on the other hand, it is then possible to hybridize positive clones with the 39mer A and B probes individually.

It is highly probable that the clones which hybridize both with the long probe and with both short 39mer probes A and B have the desired sequence. Thus, the method of constructing a long, complex oligonucleotide probe and of "rescreening" the clones using the partially complementary short DNA probes, which has been described, represents an enhancement of specificity. In addition, it is possible with the long oligonucleotide and its partially complementary short partoligonucleotides to screen genomic bands with enhanced specificity. Another advantage of the said method is that the synthesis of shorter oligonucleotides can be carried out more easily and with higher yields and accuracy. The sequence of two enzymatic reactions, namely 1) T4 polynucleotide kinase for the (γ-$^{32}$P)-ATP labeling, and 2) DNA polymerase filling-in reaction with addition of (α-$^{32}$P)-dNTP, means that it is possible to obtain higher specific activities (at least 1×10$^8$ Bq/µg DNA).

Screening of the placental cDNA with F XIIIa-specific oligonucleotides

5×10$^5$ PFU of the placental cDNA bank were examined for cDNA sequences coding for F XIIIa using the 20mer probe and the 66mer probe. This entailed 3×10$^4$ PFU being plated out with cells of the E. coli K 12 strain C 600 HFL in soft agar in 13.5 cm Petri dishes and incubated at 37° C. for 6 h. Any lysis which had taken place by this time was still incomplete. The plates were incubated in a refrigerator overnight, and the phages were transferred to nitrocellulose filters (Schleicher & Schüll, BA 85, Ref. No. 401124) (duplicates). The nitrocellulose filters and Petri dishes were marked with an injection needle in order to allow subsequent allocation. The Petri dishes were stored in a cold room during the processing of the nitrocellulose filters. The DNA on the nitrocellulose filters was denatured by placing the filters for 5 min. on filter paper (Whatman M 3) impregnated with 1.5 M NaCl, 0.5 M NaOH. The filters were then renatured in the same way using 1.5 M NaCl, 0.5 M tris (pH 8.0) and washed with 2×SSPE (0.36 M NaCl, 16 mM NaOH, 20 mM NaH$_2$PO$_4$, 2 mM EDTA). The filters were then dried in vacuo at 80° C. for 2 h. The filters were washed in 3×SSC, 0.1% SDS (20×SSC=3 M NaCl, 0.3 M Na citrate) at 65° C. for 4 h, and prehybridized at 65° C. for 4 h (prehybridization solution: 0.6 M NaCl, 0.06 M tris (pH 8.3), 6 mM EDTA, 0.2% non-ionic synthetic sucrose polymer ((R)Ficoll), 0.2% polyvinylpyrrolidone 40, 0.2% BSA, 0.1% SDS, 50 µg/ml denatured herring sperm DNA). The filters were incubated overnight with the addition of 100,000–200,000 Bq of the labeled oligonucleotide per ml of hybridization solution (as prehybridization solution but without herring sperm DNA) in beakers or in sealed polyethylene films, shaking gently. The hybridization temperature for the 20mer probe and for the 39mer probes was 42° C., and that for the 66mer probe was 47° C.

The nitrocellulose filters were washed with 6×SSC, 0.05 M sodium pyrophosphate at room temperature for 1 h and at the particular hybridization temperature for a further hour. The filters were dried and autoradiographed overnight. Signals occurring on both duplicate X-ray films were allocated to the Petri dish, and the region (about 50 plaques) was punched out with the wide end of a Pasteur pipette, and the phages were re-suspended in 1 ml of SM buffer. Positive phages were singled out over three rounds until a single clone was obtained.

A total of 5×10$^5$ PFU of the placental cDNA bank was examined in several passages. 17 signals were identified on duplicate filters. Further screening under more stringent conditions resulted in 7 signals still being positive. Of these 7 PFU only one PFU showed a positive signal both after hybridization with the 20mer and 66mer probes and with the 39mer probes A and B. This clone—called λgt10-12 hereinafter—has a sequence of 1704 base-pairs coding for F XIIIa and having an internal EcoRI cleavage site. Southern blot analysis shows that the smaller EcoRI fragment of 540 base-pairs hybridizes with the 20mer DNA probe, and the larger fragment of 1164 base-pairs hybridizes with the 66mer DNA probe.

On rescreening, it emerged from the Southern blot that there is more reaction with the 39mer probe A than with the 39mer probe B. Sequence analysis of the clone λgt10-12 showed subsequently that, over the entire length of the 66mer probe, there are only seven mismatches to the sequence found for F XIIIa (Table 2). The seven mismatches are distributed as follows: there are three in the 39mer A probe and five mismatches in the 39mer B probe (one mismatch occurs in the overlapping region, and thus is common to both). The five mismatches in the 39mer B probe are clustered, which is possibly the reason for the weaker hybridization signals in the case of the 39mer B probe.

Screening of the placental cDNA with nick-translated EcoRI fragments

The two subcloned EcoRI fragments, which were 540 base-pairs and 1164 base-pairs in length, were cloned into the EcoRI cleavage site of the commercially available vector pUC8 (1164 bp=pUC8-12.1 and 540 bp=pUC8-12.2) and were isolated therefrom preparatively with EcoRI, and nick-translated in the presence of (α-$^{32}$P)-dNTP. The specific activity of both fragments was 1×10$^8$ Bq/µg DNA. Using the ($^{32}$P)-labeled fragments in several passages, about 1×10$^6$ recombinant phages of the placental cDNA bank were examined (hybridization temperature 65° C.) and thus 13 hybridizing phages were identified. The phages were singled out over three rounds until a single homogeneous phage preparation was obtained. 20 ml lysates of each phage were set up, and the DNA was extracted. The DNA was digested with EcoRI and fractionated on a 1% agarose gel. The gel was subjected to the Southern blot technique, and the nitrocellulose filter was hybridized with the labeled 540 bp EcoRI fragment. Eleven phages showed hybridization signals. The nitrocellulose filter was boiled and hybridized with the nick-translated 1164 bp EcoRI fragment. Nine phages showed hybridization signals.

It was possible to identify, on the basis of the size of the hybridizing fragments, clones which, in comparison with λgt10-12, expand both towards the 5' end such as λgt10-20 and towards the 3' end such as λgt10-11. It was possible by use of these clones to determine the complete F XIIIa cDNA sequence. It was possible to combine part-sequences which were present by use of internal restriction sites or by hybridization of overlapping sequences. The complete cDNA sequence can be ligated into expression vectors and expressed in suitable prokaryotic or eukaryotic systems.

DNA sequence analysis

The phage clone λgt10-12 was multiplied, and the DNA was extracted. The two EcoRI fragments were isolated and cloned into the EcoRI site of the plasmid vector pUC8. pUC8-12.1 has the 1164 base-pair fragment, and pUC8-12.2 has the 540 base-pair fragment. In order to isolate the entire fragment comprising 1704 base-pairs, λgt10-12 was partially digested with EcoRI, and the 1704 base-pair band was isolated and cloned into the EcoRI site of pIC19H (Marsh et al., Gene 32 (1984) 481–485). The resulting plasmid is called pIC19H-12.

It was possible by cloning Sau 3A, AluI and TaqI sub-fragments of the clones pUC8-12.1, pUC8-12.2 and pIC19H-12 into pUC plasmids and M13 phages, followed by sequencing of the relevant regions using the enzymatic dideoxy method of Sanger and the chemical method of Maxam and Gilbert, to determine the sequence of the 1704 bp fragment (Table 3). The sequence shows only one open reading frame and codes for the first 542 amino acids of the factor XIIIa molecule.

Restriction analysis of the clone λgt10-12 or pIC19H-12 and of the clones λgt10-11 and λgt10-20 was carried out both by suitable single and multiple digestions and by partial digestion of ($^{32}$-P)-labeled DNA fragments by the method of Smith and Birnstiel (Smith, H. O. and Birnstiel, M. L., Nucleic Acids Res. 3 (1976) 2387–2398) (FIG. 1).

The clone λgt10-11 has a fragment which is 2432 bp in size and has an internal EcoRI cleavage site. This fragment overlaps by 237 bp at the 3' end the cDNA fragment from λgt10-12, and comprises the remaining 570 bp of the coding sequence plus 1625 bp of the non-coding region including a poly(A) sequence of 89 bases. The clone λgt10-20 with a cDNA fragment about 700 bp in size also has at the 5' end 6 bases more (GAG GAA . . . ) than λgt10-12.

Figure 2:
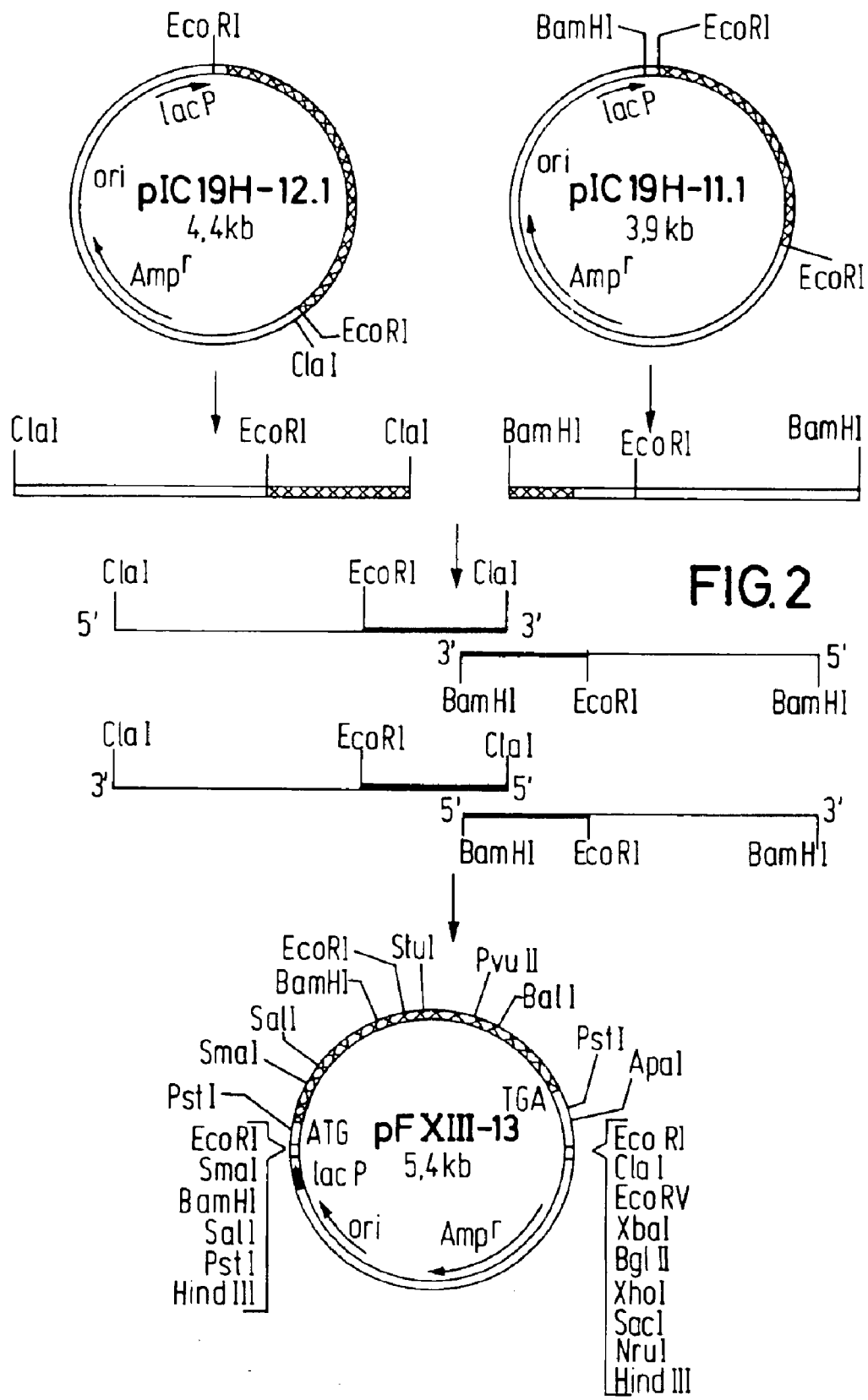
FIG. 2 shows the construction of the expression plasmid pFXIII-13. For clarity, in this figure the starting plasmids pIC19H-12.1 and pIC19H-11.1, as well as the DNA fragments located immediately below them, are represented by double lines, as is the product pFXIII-13 constructed from the single-stranded fragments.

2. Preparation of a clone which can be expressed and contains the entire cDNA coding for F XIIIa The starting clones λgt10-11 and λgt10-12 were used to obtain a plasmid which contains the entire coding region of the F XIIIa cDNA. With the aid of partial EcoRI digestion, the insertion, comprising 1704 base-pairs, of λgt10-12 was cloned into the EcoRI site of pIC19H (Marsh et al., loc. cit.). The resulting plasmid pIC19H-12.1 was used subsequently (see FIG. 2). The clone λgt10-11 has an insertion 2432 base-pairs in size and has an internal EcoRI cleavage site. The left ("5'-terminal") EcoRI fragment, which is 1224 base-pairs in size and embraces the C-terminal 570 base-pairs of the coding sequence plus 654 base-pairs of the 3' non-coding region, was likewise cloned into the EcoRI cleavage site of pIC19H. The resulting plasmid pIC19H-11.1 was used subsequently (FIG. 2). The plasmids pIC19H-12.1 and pIC19H-11.1 have the coding region for F XIIIa in the same orientation in the vector and have an overlapping region which comprises 237 base-pairs. This overlapping region was used to construct from the part-clones pIC19N-12.1 and pIC19H-11.1 a clone which embraces the entire coding region. This entailed preparation, from the two plasmids mentioned, of partially single-stranded heteroduplex molecules by hybridization in vitro (FIG. 2) and transformation of the reaction mixture into E. coli. By utilization of the repair mechanisms of the bacterium (3'→5' exonuclease activity, 5'→3' polymerization activity of the enzyme DNA p lymerase I), a plasmid with the entire coding region was obtained.

Specifically, this entailed 1 µg of the DNA of each of the plasmids pIC19H-12.1 (ClaI-digested) and pIC19H-11.1 (BamHI-digested) being mixed and precipitated with ethanol. The DNA was dried in vacuo, taken up in 20 µl of $H_2O$ and, after addition of 5 µl of 1 N NaOH, incubated at room temperature for 10 minutes. The following were then added in the sequence indicated: 200 µl of $H_2O$, 25 µl of 1 M tris.HCl (pH 8.0) and 50 µl of 0.1 N HCl. The reaction mixture was incubated at 65° C. for 3 hours, precipitated with ethanol, and dried. The DNA was resuspended in 20 µl of $H_2O$ and transformed by known methods into E. coli, and the cells were plated onto LB-amp plates and incubated overnight. Of the total of 96 ampicillin-resistant clones, 24 clones were worked up by the alkali method (Birnboim and Doly, Nucl. Acid Res. 7 (1979) 1513–1523), and the plasmids were characterized by restriction endonucleolysis with HindIII, EcoRI, BamHI and PvuII. Six plasmids showed the expected restriction pattern. One of these plasmids, pFXIII-13 (FIG. 2), was characterized in detail. This entailed the StuI (position 1225)-PvuII (position 1870) fragment, which embraces the 237 base-pair overlapping region, being sequenced, and the DNA sequence was confirmed as correct. The plasmid pFXIII-13 comprises 2693 base-pairs of FXIIIa cDNA, of which 78 bp are of the 5' non-translated region, 2196 bp are the entire coding region, and 419 bp are of the 3' non-translated region. pFXIII-13 was the starting plasmid for all subsequent expression experiments.

3. Expression of biologically active factor XIIIa in E. coli a) Construction of F XIIIa expression plasmids pFXIII-13 has the F XIIIa cDNA insert in the correct orientation with respect to the lac promoter and in the correct reading frame with respect to the lacZ α-peptide. pFXIII-13 is thus able to induce the synthesis of a F XIIIa fusion protein in E. coli. The molecular weight of this protein comprises the 732 amino acids of natural F XIIIa together with 16 vector-coded amino acids plus 28 amino acids specified by the 5' non-coding region. These additional 44 amino acids are located at the N-terminal end of the fusion protein. The expected molecular weight of this protein is 85,250 D (Tab. 4).

Figure 3A:
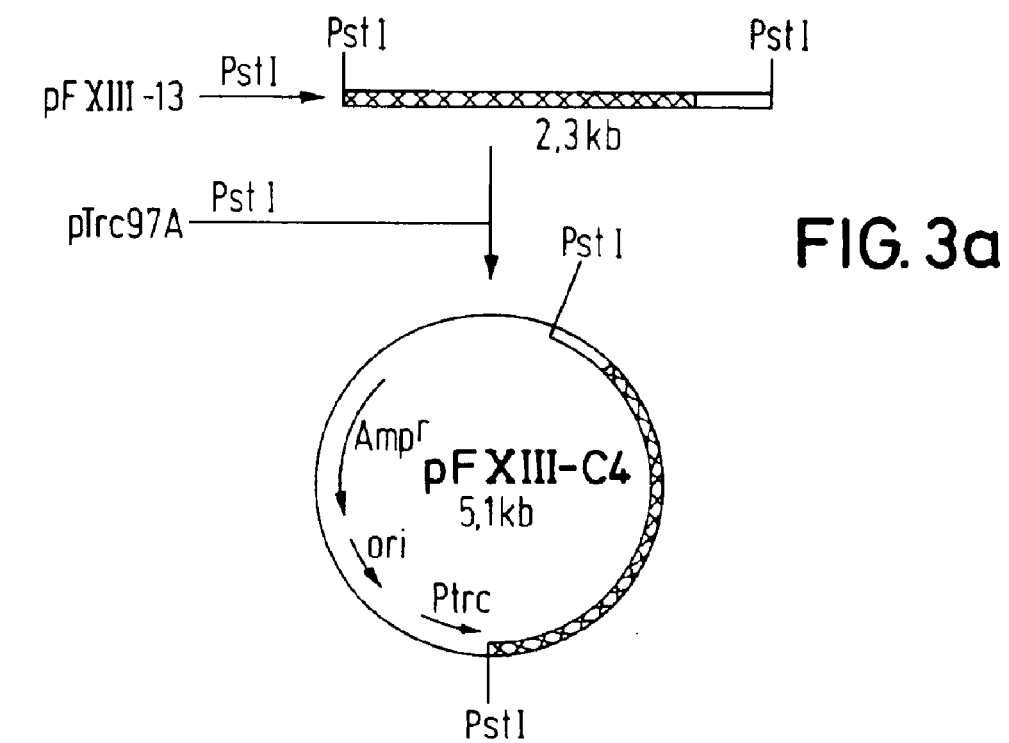
FIG. 3 is a diagram of the construction of the plasmid pTrc97A, FIG. 3a that of pFXIII-C4 from pTrc97A and pFXIII-13, and finally FIG. 3b the construction of pMB259 from pFXIII-13 and the known plasmids pIC20H and pBD2.
Figure 3:
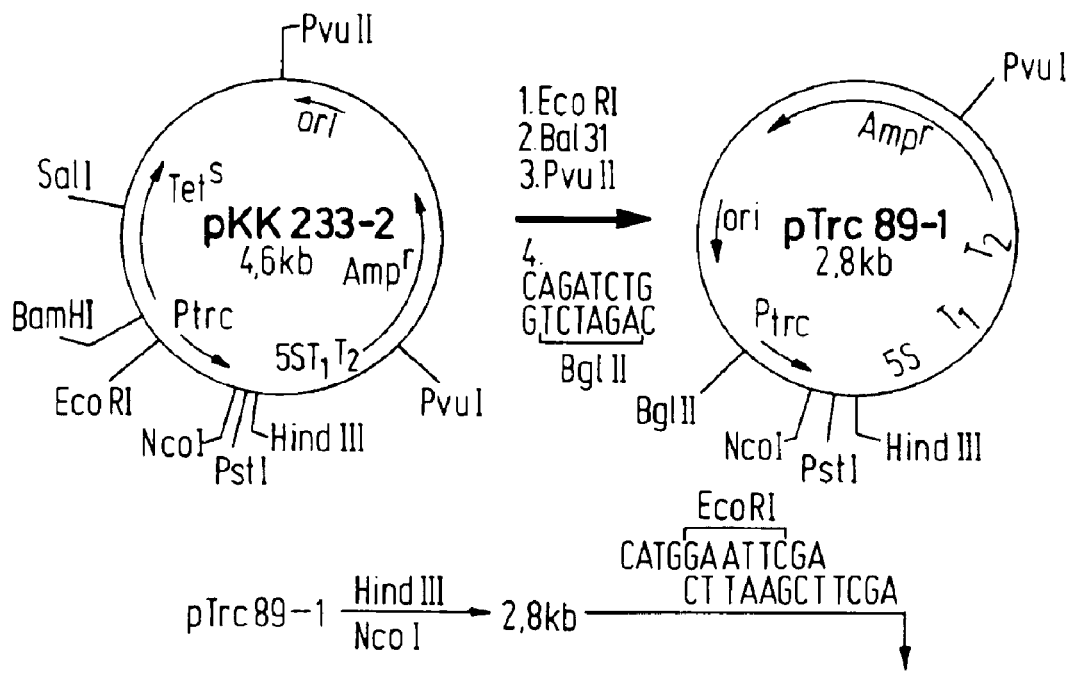
Figure 3:
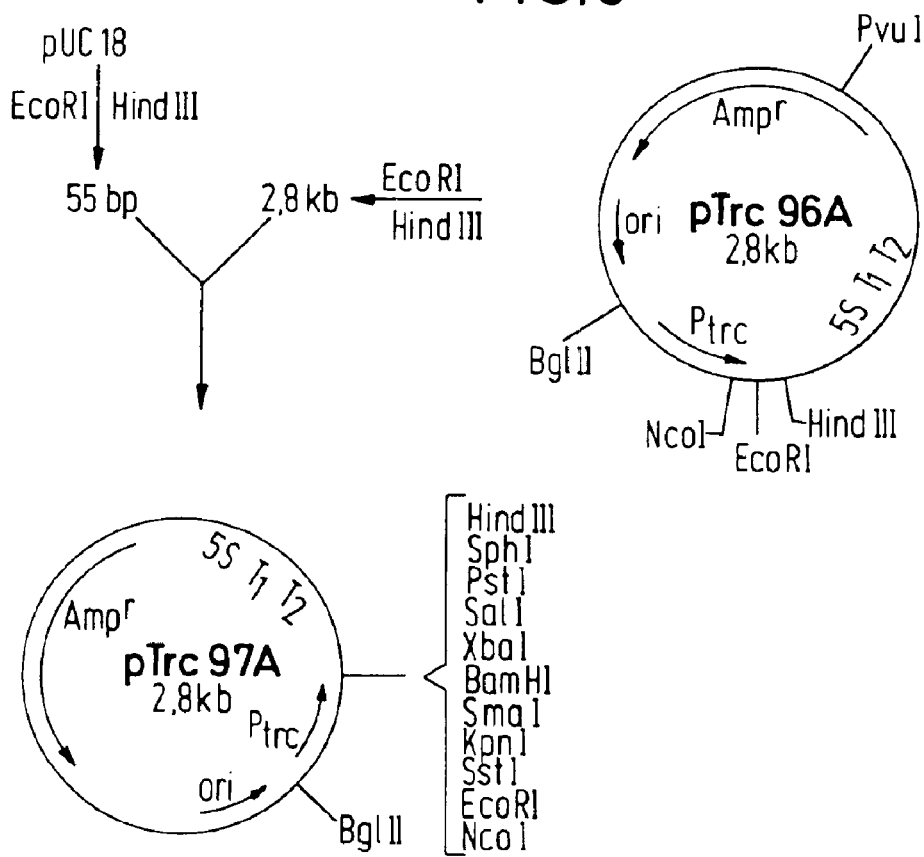

An expression plasmid which uses in place of the lac promoter a more efficient trp/lac hybrid promoter was subsequently constructed. For this, pKK233-2 (Amann and Brosius, Gene 40 (1985), 183–190) was cut with EcoRI and treated with Bal31 (FIG. 3). The DNA was then cut with PvuII, and the fragment 2800 base-pairs in size was purified on a PAA gel. This fragment was religated in the presence of a BglII linker (5'-CAGATCTG). The resulting plasmid pTrc89-1 (FIG. 3) was cut with NcoI and HindIII, and the synthetic linker

5' CATGGAATTCGA 3'
3' CTTAAGCTTCGA 5' was incubated together with the 2800 base-pair fragment in a ligase mixture. The resulting plasmid, pTrc96A (FIG. 3), was cut with EcoRI and HindIII, and the fragment 2800 base-pairs in size was gel-purified and ligated with the EcoRI-HindIII linker which is 55 base-pairs in size from pUC18. The resulting plasmid is pTrc97A (FIG. 3). In contrast to pKK233-2, pTrc97A has, downstream of the NcoI site which occurs only once in the plasmid, the polylinker from pUC18 and thus has numerous cloning sites.

The FXIIIa cDNA cloned into pFXIII-13 has a PstI site 21 base-pairs 5' away from the ATG initiation codon (position 61). The next PstI site is located in the 3' untranslated region (position 2398). The PstI fragment which is 2337 base-pairs long was isolated from pFXIII-13 and ligated into the PstI site of pTrc97A. The resulting plasmid with the PstI fragment in the desired orientation is pFXIII-C4 (FIG. 3a). The expected FXIII molecule specified by pFXIII-C4 has 22 additional N-terminal amino acids, 15 of them being vector-coded and 7 being specified by the 5' non-coding region of the F XIII cDNA. The expected molecular weight of this protein is 82,830 D (Tab. 4).

Figure 3B:
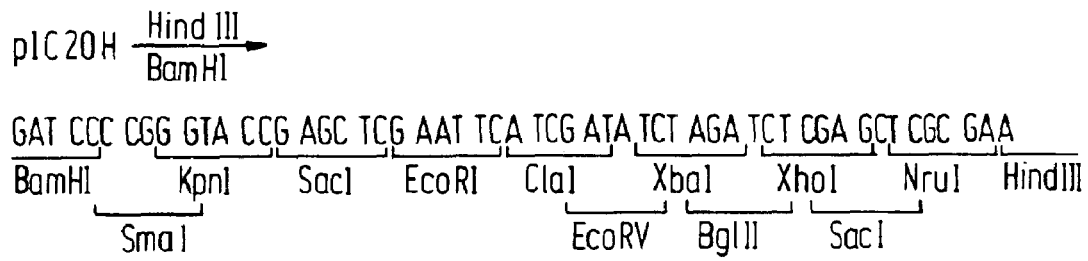
Figure 3B:
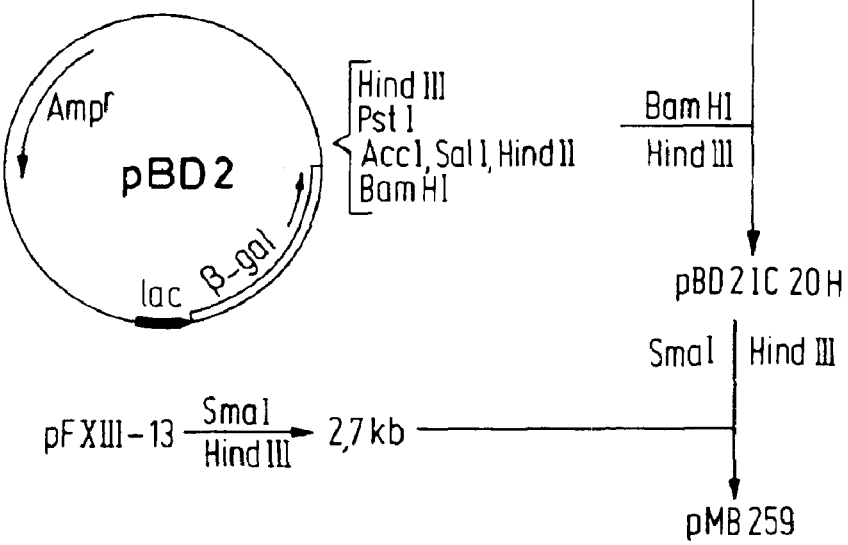

Use of thrombin to cleave off the 37 amino-terminal amino acids converts the F XIIIa into the active form. Since such a F XIIIa molecule which has already been activated is of therapeutic interest, an attempt was made to express in E. coli a F XIIIa that can be shortened by thrombin cleavage. In order to obtain a high yield the cloning was carried out in such a way that the shortened F XIIIa is expressed in the form of a hybrid protein, fused to an E. coli β-galactosidase fragment. The SmaI-HindIII fragment which is about 2700 bp in size from pFXIII-13 was isolated and ligated into pBD21C20H which had been hydrolyzed with SmaI and HindIII. In the new plasmid pMB259 (FIG. 3b), the coding region of the cDNA for F XIIIa from amino acid $Pro_{37}$ to $Met_{732}$ is located in the reading frame applying to the 375 aminoterminal amino acids of the β-galactosidase, and it has the thrombin cleavage site $Arg_{38}/Gly_{39}$ so that it is possible to obtain activated F XIIIa by thrombin cleavage from the synthesized fusion proteins.

The expression vector pBD2IC20H had been constructed by ligating the polylinker region, which comprises 58 bp, of the plasmid pIC20H (Marsh et al., loc. cit.) as BamHI-HindIII fragment in pBD2 (Broker, Gene Anal. Techn. 3 (1986) 53–57) which has the lac promoter.

b) Expression

It was found that E. coli cells of the strain D29A1 which are transformed with pFXIII-13, with pFXIII-C4 or with pMB259 are able to synthesize the expected F XIIIa proteins. The expression of F XIII by the plasmids pFXIII-13, pMB 259 and pFXIII-C4 can be induced with IPTG. Comparison of protein extracts after IPTG induction of E. coli D29A1 (pFXIII-13) and D29A1 (pFXIII-C4) on PAA gels stained with Coomassie blue showed the expected molecular weights of the F XIII fusion proteins. The estimated expression of the "44aa FXIII fusion protein" is about 5 times that of the "22aa FXIII fusion protein".

It was also found that the F XIIIa molecules specified by pFXIII-13 and pFXIII-C4 have biological activity. In contrast, no F XIII activity was found in E. coli D29A1 control extracts. The activity found in the clot stability assay (Karges, in Bergmeier, Methods of Enzymatic Analysis, Volume 5, Enzymes 3: Peptidases, Proteinases and their Inhibitors, pages 400–410) is 5 µg/l for E. coli D29A1 (pFXIII-13), based on the E. coli culture ($OD_{250}$=1.5), and is 15 µg/l for D29A1 (pFXIII-C4).

The amount of factor XIII found in the F XIIIa-specific ELISA is 1.5 mg/l, based on the E. coli culture, for pFXIII- 13 and is 3 mg/l for pFXIII-C4. The discrepancy between the amounts of F XIII measured in the biological assay and in the ELISA derives from the fact that the major part (>90%) of F XIII in the *E. coli* cell is in the form of an insoluble precipitate which is biologically inactive and dissolves only in 7 M urea. The soluble fraction of the F XIII molecules present in *E. coli* extracts shows in the Ouchterlony test (Ouchterlony, Progr. Allergy 5 (1958) 1) a precipitation curve which is substantially identical to that of F XIII isolated from placenta.

The expression of eukaryotic proteins in *E. coli* in the form of insoluble protein aggregates has already been described for several proteins. These proteins can be dissolved out of such aggregates using a chaotropic agent and can be converted by suitable renaturing conditions into their biologically active form.

4. Expression of F XIII in yeasts

The synthesis of biologically active F XIII obtained by gene manipulation from yeasts was achieved by incorporating the cDNA coding for F XIII into expression vectors which are able to replicate autonomously in yeasts. It was possible to isolate F XIII-active protein from extracts of the recombinant clones.

The conditions for growing yeasts and the molecular biological methods are described in Dillon et al., Recombinant DNA Methodology, John Wiley & Sons, New York (1985) and in Maniatis et al., loc. cit.

Figure 4:
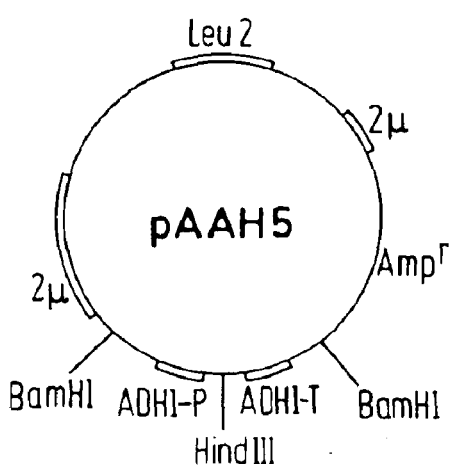
FIG. 4 is a diagram of the construction of the plasmid pMB240 from pFXIII-13 and the known plasmid pAAH5.
Figure 4:
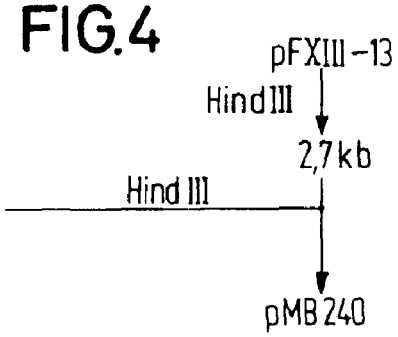

The F XIII cDNA was isolated from the vector pFXIII-13 as a HindIII fragment about 2700 bp in size, and was cloned into the HindIII site of the vector pAAH5 (Ammerer, Meth. Enzymol. 101 (1983), 192–201). Thus, the F XIII cDNA in the resulting plasmid pMB240 (FIG. 4) is under the control of the strong ADHI promotor which contains the gene expression signals of alcohol dehydrogenase. The plasmid pMB240 was transformed into baker's yeast, *Saccharomyces cerevisiae*, strain Leu 2-3, Pep 4-3, by the method of Itoh et al. (J. Bacteriol. 153 (1983), 163–168) and Leu$^+$ transformants were selected on YNB minimal medium. One colony of transformed yeast cells was used to inoculate a liquid culture with YNB medium. After growth at 30° C. for two days, transfer into complex YPB medium was carried out and, after a further three days, the cells were removed by centrifugation and were disrupted with a glass bead mill in isotonic saline solution containing 100 mM sodium citrate (pH 7.2). The cell extract was subjected to high-speed centrifugation in a Sorvall high-speed centrifuge, in a SS34 rotor, at 20,000 rpm and 4° C. for 1 hour.

The cell-free supernatant of *S. cerevisiae* (pMB240) was analyzed by the Western blot method. In addition to a band which can be detected in the same position as F XIII from placenta, a protein of about 116,000 D reacted specifically with the anti-F XIII serum used. This proves that part of the F XIII formed in yeasts is glycosylated. The glycosylation of proteins is often a factor prolonging the half-life of proteins, especially plasma proteins. In addition, carbohydrate sidechains may increase the activity or extend the duration of the action of plasma proteins, for example antithrombin III. A F XIII which is expressed in yeast and which, in contrast to F XIII obtained from placenta, is glycosylated or has undergone posttranslatimal modification in some other way can have, owing to an increased activity, advantages over F XIII from placenta.

The cell-free supernatant was examined for F XIII by an ELISA, and the F XIII concentration was found to be 150 ng/ml, based on the yeast culture. The biological activity of F XIII was determined by the method of Karges, loc. cit., and confirmed the concentrations measured in the ELISA. It was possible to rule out a non-specific F XIII-like activity by yeast proteins because the biological activity of the F XIII obtained from baker's yeast could be specifically inhibited by anti-F XIII antibodies.

Figure 5:
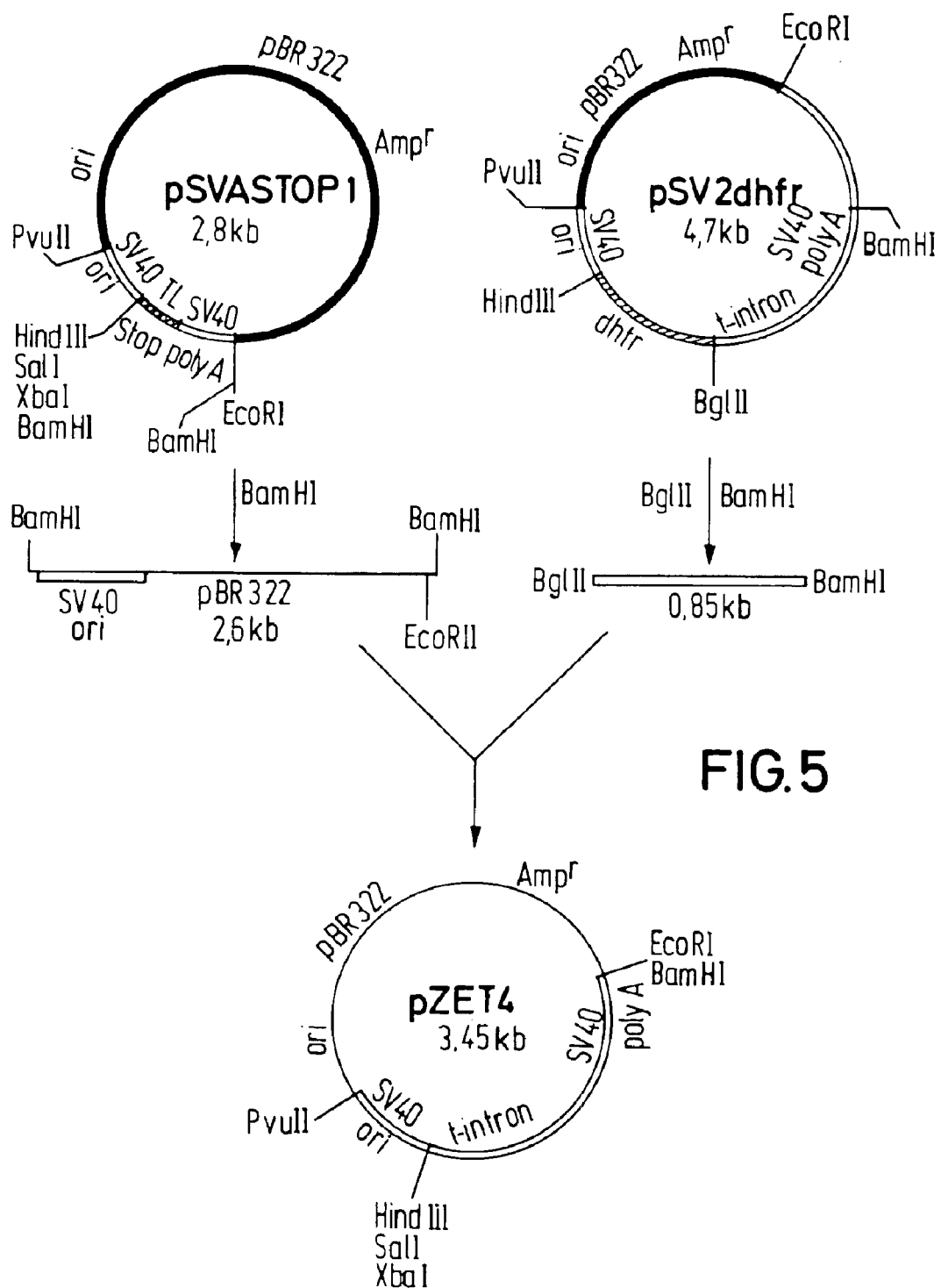
FIG. 5 shows the construction of pZET4 from the known plasmid pSV2dhfr and the plasmid pSVA STOP1.
Figure 5A:
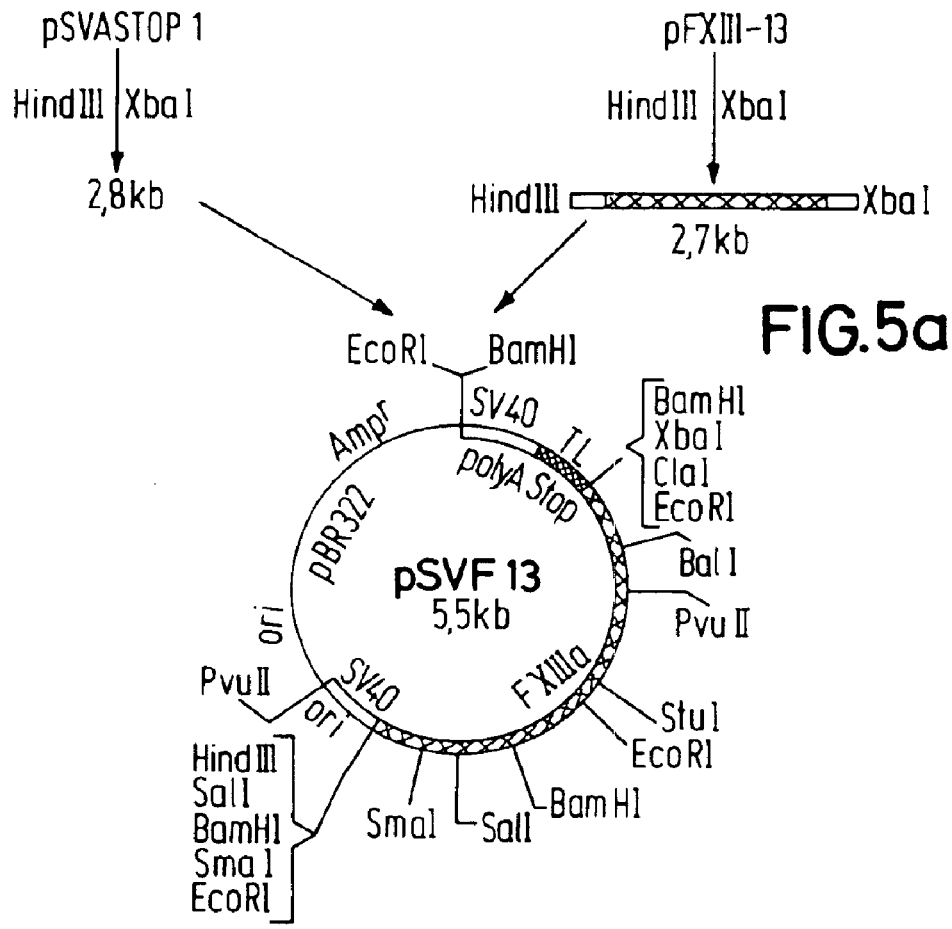
FIG. 5a shows the construction of pSVF13 from pSVA STOP1 and pFXIII-13.
Figure 5B:
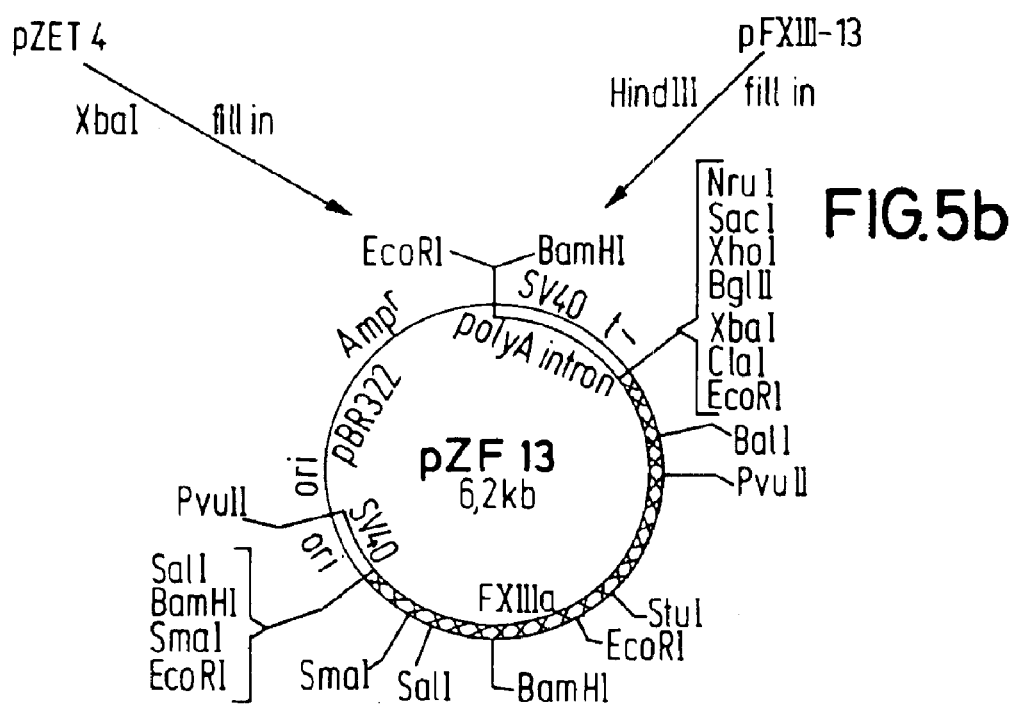
FIG. 5b shows the construction of pZF13 from pZET4 and pFXIII-13, and finally
Figure 5C:
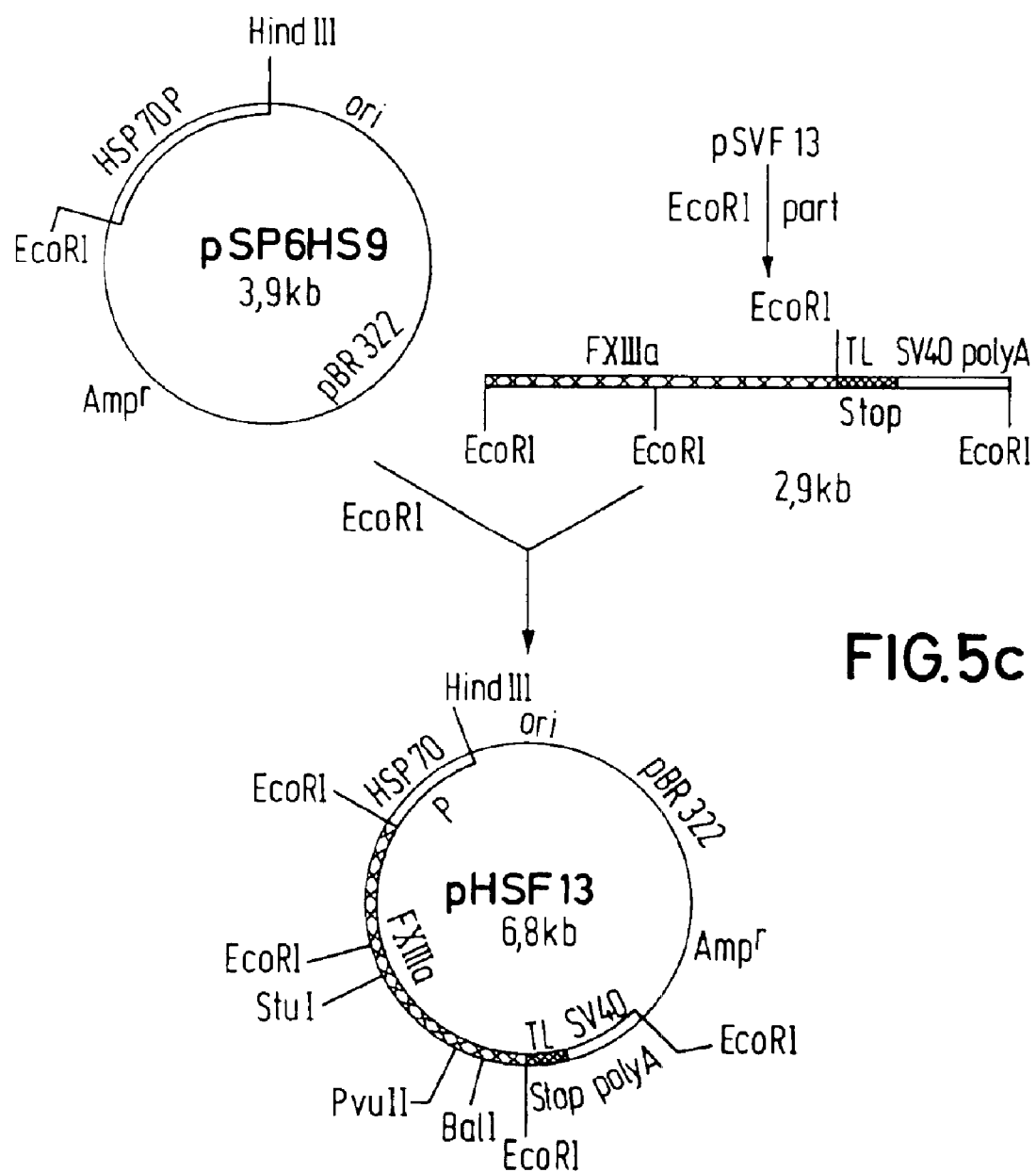
FIG. 5c shows the construction of pHSF13 from pSVF13 and the known plasmid pSP6HS9.

5. Expression of F XIIIa in animal cells a) Construction of expression vectors for animal cells The expression vector pSVA STOP1 is proposed in German Patent Application P 36 24 453.8 (Example 1 of this application, which relates to the synthesis of this vector, has been extracted and is reproduced in the Appendix). Apart from this plasmid, use was made of the vectors pZET4 (see below) and pSP6HS9, which has the *Drosophila* heat shock protein 70 promotor (Wurm et al., Proc. Natl. Acad. Sci. USA 83 (1986) 5414–5418), for the expression of F XIIIa in animal cells.

pZET4 (FIG. 5): the plasmid pSVA STOP1 was cut with BamHI, and the vector fragment which is 2.6 kb in size and has the SV40 early promotor was isolated. The BglII-BamHI fragment 0.85 kb in size from pSV2dhfr (Lee et al., Nature 294 (1981) 228–232) was ligated into the vector which had been pretreated in this way, which resulted in the plasmid pZET4. Located on the 0.85 kb fragment from pSV2dhfr are mRNA splice sites from exon-intron joins, and the polyadenylation site of the gene for the t antigen from the SV40 DNA.

b) Construction of F XIIIa expression vectors for animal cells pSVF13 (FIG. 5a): the expression vector pSVA STOP1 was cut with HindIII and XbaI. A HindIII-XbaI fragment, about 2.7 kb in size and having the F XIIIa cDNA, from pFXIII-13, was ligated into the vector which had been treated in this way. The F XIIIa transcription unit on pSVF13 has no mRNA splice sites.

pZF13 (FIG. 5b): a HindIII fragment about 2.7 kb in size and containing the F XIIIa cDNA was isolated from the plasmid pFXIII-13. The resulting 5' protruding end was eliminated by filling in the complementary strand with DNA polymerase I (Klenow fragment). The expression vector pZET4 was linearized by cutting at the unique XbaI site. The resulting 5' protruding end was likewise eliminated by filling in the complementary strand with DNA polymerase I (Klenow fragment). Ligation of the filled-in vector with the filled-in F XIIIa cDNA fragment results in the F XIIIa expression plasmid pZF13. As in pSVF13, the F XIIIa cDNA is under the transcriptional control of the SV40 early promoter but is provided with mRNA splice sites.

pHSF13 (FIG. 5c): the plasmid pSVF13 was partially digested with EcoRI, and a fragment about 2.9 kb in size and having the F XIIIa cDNA followed by the SV40 polyadenylation site for early transcripts was isolated. This fragment was ligated into the unique EcoRI site of the plasmid pSP6HS9 downstream of the heat shock protein 70 promotor.

c) DHFR expression vectors for the cotransfection of CHO (Chinese hamster ovary) dhfr$^-$ cells Either the DHFR vector pSV2dhfr (Lee et al., loc. cit.) or the promotorless DHFR plasmid pSV0Adhfr (German Patent Application P 36 24 453.8, see Appendix) was used for the cotransfection with the described F XIIIa expression vectors in CHO dhfr$^-$ cells. Both vectors have the DHFR cDNA from the mouse.

d) Vector conferring G418 resistance for the cotransfection of BHK (baby hamster kidney) cells The F XIIIa expression vectors which have been described were cotransfected with the vector pRMH140 (Hudziak et al., Cell 31 (1982), 137–146) in BHK cells.

e) Expression of F XIIIa in CHO cells

Cotransfection of the plasmid pZF13 with the DHFR vector pSV2dhfr, and of the expression plasmid pSVF13 together with the DHFR vector pSVOAdhfr, was carried out using the calcium phosphate precipitation method (Graham and van der Eb, Virology 52 (1973), 456–467) in CHO dhfr⁻ cells. This entailed 20 µg of the particular F XIIIa expression plasmid (pZF13 or pSVF13) being mixed and coprecipitated with 5 µg of the DHFR vectors (pSV2dhfr or pSVOAdhfr). The coprecipitate was used for transfection as described above ($0.5 \times 10^6$ cells in a 25 cm² culture bottle). After 3 days, the cells were trypsinized, transferred into three 60 mm Petri dishes and mixed with selection medium (containing no glycine, hypoxanthine or thymidine). The only cells which survive under these conditions are those which have undergone stable transfection with the DHFR gene. Colonies of transfected cells become visible on the Petri dishes after 1–3 weeks. The following transfection rates were achieved by this method:

pSV2dhfr $5 \times 10^{-5}$/plate
pSVOAdhfr $1 \times 10^{-5}$/plate

Individual clones were isolated and multiplied in a medium containing no glycine, hypoxanthine or thymidine.

A specific ELISA with a lower detection limit of about 3 ng/ml was used to detect F XIIIa in culture supernatants and cell lysates of the individual clones. Culture supernatants were used as such in the ELISA. The cell lysates were prepared as follows: Confluent cells in 25 cm² culture bottles were washed twice in 40 mM tris.HCl (pH 7.4), 1 mM EDTA, 150 mM NaCl, taken up in 150 µl of 0.25 M tris.HCl (pH 7.8), 5 mM DTT, 2% glycerol, 0.2% detergent (Triton X100), and lyzed by freezing and thawing three times.

In soluble constituents of the cells were removed by centrifugation. The lysate was diluted 1:2.5 for use in the ELISA. The detection method which has been described was applied to 17 clones for the combination of the plasmids pZF13/pSV2dhfr, and one clone expressing F XIIIa (CH0 59-5-C7) was found. After cotransfection with the plasmids pSVF13/pSVOAdhfr and analysis of 12 clones, a further F XIIIa-expressing clone (CH0 60-3-C1) was detected. With both the positive clones it was possible to detect F XIIIa in the medium and in the lysate in the same relative amounts. In order to determine quantitatively the expression rate of the lines producing F XIIIa the following standard procedure was carried out:

$0.5 \times 10^6$ cells were plated out in 5 ml medium in 25 cm² culture bottles. The medium was changed after 24 hours (5 ml). Another 24 hours later the medium was removed, the cell count was determined, and lysates were prepared. For all the expression rates (ng/$10^6$ cells/24 h) stated hereinafter, the cell count per 25 cm² bottle at the end of the test was $1 \pm 0.25 \times 10^6$ cells. The table which follows shows the expression rate of the basic clones tested in the manner described:

|  | extracellular (ng/$10^6$ cells/24 h) | intracellular (ng/$10^6$ cells/24 h) |
|---|---|---|
| CHO 59-5-C7 | 12 | 9 |
| CHO 60-3-C1 | 17 | 13 |

On SDS electrophoresis followed by F XIIIa-specific immunoblotting of lysates and supernatants of the clone CH0 59-5-C7 and the clone CH0 60-3-C1, in each case one band with the molecular weight of the protein isolated from human placenta showed a reaction.

The clone CH0 59-5-C7 was exposed to increasing concentrations of methotrexate (Mtx) for gene amplification. Starting with a concentration of 10 nM Mtx and a 4-transfer adaptation time, the Mtx concentration in the medium was increased to 50 nM. The following expression rates were determined in the standard procedure:

| Mtx (nM) | extracellular (ng/$10^6$ cells/24 h) | intracellular (ng/$10^6$ cells/24 h) |
|---|---|---|
| 0 | 12 | 9 |
| 10 | 19 | 16 |
| 50 | 38 | 66 | f) Expression of F XIIIa in BHK cells

20 µg of each of the F XIIIa expression plasmids pZF13, pSVF13 and pHSF13 were cotransfected with 5 µg of the plasmid pRMH140 which codes for G418 resistance, by the calcium phosphate precipitation method described in example 5e) in BHK cells. After 3 days, the cells were trypsinized, transferred into three 60 mm Petri dishes and mixed with selection medium containing 400 µg/ml G418. After 12 days about 200–300 G418 resistant colonies had grown in each Petri dish. The total number of clones was trypsinized and subjected to transfers as combined clone (CC) in 25 cm² culture bottles (5 ml of medium).

In the case of cells transfected with pZF13 and pSVF13, where an 80–100% confluence had been reached F XIIIa was determined in the medium and in the relevant lysate (see example 5e)) using a specific ELISA. Combined clones which had been transfected with pHSF13 and had likewise reached 80–100% confluence were mixed with fresh medium which had been preheated to 42° C. and were incubated at 42° C. for one hour. After another replacement of the medium with fresh medium equilibrated at 37° C., the cells were maintained at 37° C. for 24 hours. The medium and lysates were then examined for their content of F XIIIa as described above. The table which follows summarizes the cellular distribution of F XIIIa for the various combined clones.

|  | extracellular (ng) | intracellular (ng) |
|---|---|---|
| BHK-MK1 (pZF13) | 65 | 22 |
| BHK-MK2 (pZF13) | 80 | 20 |
| BHK-MK3 (pSVF13) | 85 | 18 |
| BHK-MK5 (pHSF13) | 170 | 11 |

The expression rates relating to the F XIIIa present in the medium were determined for the individual combined clones by the standard procedure described in example 5e). For all the expression rates (ng/$10^6$ cells/24 h) stated hereinafter, the cell count per 25 cm² bottle at the end of the test was $4.5 \pm 0.5 \times 10^6$ cells.

|  | extracellular (ng/$10^6$ cells/24 h) |
|---|---|
| BHK-MK1 (pZF13) | 3.4 |
| BHK-MK2 (pZF13) | 5.6 |
| BHK-MK5 (pHSF13) | 3.8 |
| BHK-MK6 (pHSF13) | 3.8 |

Since the transfected BHK lines described hitherto have been mixed populations including cells which were not producing or differed in their expression rates, it was subsequently attempted to isolate genetically uniform cell lines with high expression rates by singling out clones. For this purpose, cells from the particular combined clone were placed on microtiter plates in a concentration of 1 cell/well, 2 cells/well or 4 cells/well. Supernatants from wells in which only one clone had grown were analyzed by the F XIIIa-specific ELISA. The clones with the highest expression rates were multiplied in 25 cm² culture bottles, and their expression rates were investigated by the standard procedure described above. The table which follows shows the expression rate of clones obtained by singling out BHK-MK1 (pZF13) in the manner described.

|  | extracellular (ng/10⁶ cells/24 h) |
|---|---|
| BHK MK1 (pZF13) | 3.4 |
| BHK MK1-A12 (pZF13) | 8 |
| BHK MK1-E2 (pZF13) | 25 |
| BHK MK1-F12 (pZF13) | 14 |
| BHK MK1-C1 (pZF13) | 22 |

It was also shown, taking the example of the BHK cell line MK1-E2, that the F XIIIa molecules synthesized by these cells have biological activity. 10⁸ cells of the BHK MK1-E2 line and of the non-transfected BHK line which was used (negative control) were taken up in 1.5 ml of 0.25 M tris.HCl (pH 7.8) containing 2% glycerol. The cells were lyzed by freezing and thawing three times, followed by treatment in a Dounce homogenizer. After removal of insoluble constituents by centrifugation, the lysate was used in the biological assay (see example 3). The following F XIIIa activities were found:

| BHK MK1-E2 | 0.06 units/10⁸ cells |
|---|---|
| BHK (not transfected) | 0 units/10⁸ cells |

TABLE 1

| 20mer probe, 48-fold degenerate | | | | | | | |
|---|---|---|---|---|---|---|---|
| Amino acid sequence | Met | Met | Asp | Ile | Thr | Asp | Thr |
| DNA probe | ATG | ATG | GAT | ATT | ACT | GAT | AC |
|  |  |  | C | C | A | C |  |
|  |  |  |  | A | C |  |  |
|  |  |  |  |  | G |  |  |

TABLE 2

| 66mer probe, non-degenerate | | | | | | | | | | | |
|---|---|---|---|---|---|---|---|---|---|---|---|
| Amino acid # | 1 | 2 | 3 | 4 | 5 | 6 | 7 | 8 | 9 | 10 | 11 |
| Amin acid sequence | Tyr | Gly | Gln | Phe | Glu | Asp | Gly | Ile | Leu | Asp | Thr |
| Possible mRNA sequences | UAU | GGU | CAA | UUU | GAA | GAU | GGU | AUU | UUA | GAU | ACU |
|  | UAC | GGC | CAG | UUC | GAG | GAC | GGC | AUC | UUG | GAC | ACC |
|  |  | GGA |  |  |  |  | GGA | AUA | CUU |  | ACA |
|  |  | GGG |  |  |  |  | GGG |  | CUC |  | ACG |
|  |  |  |  |  |  |  |  |  | CUA |  |  |
|  |  |  |  |  |  |  |  |  | CUG |  |  |
| 66mer probe | TAT | GGC | CAG | TTT | GAG | GAT | GGC | ATC | CTG | GAC | ACC |
| Sequenc found | TAT | GGT | CAG | TTT | GAA | GAT | GGC | ATC | CTG | GAC | ACT |
| Amino acid # | 12 | 13 | 14 | 15 | 16 | 17 | 18 | 19 | 20 | 21 | 22 |
| Amin acid sequence | Cys | Leu | Tyr | Val | Met | Asp | Arg | Ala | Gln | Met | Asp |
| Possible mRNA sequences | UGU | UUA | UAU | GUU | AUG | GAU | CGU | GCU | CAA | AUG | GAU |
|  | UGC | UUG | UAC | GUC |  | GAC | CCG | GCG | CAG |  | GAC |
|  |  | CUU |  | GUA |  |  | CGA | GCA |  |  |  |
|  |  | CUC |  | GUG |  |  | CGG | GCG |  |  |  |
|  |  | CUA |  |  |  |  | AGA |  |  |  |  |
|  |  | CUG |  |  |  |  | AGG |  |  |  |  |
| 66mer probe | TGC | CTG | TAT | GTG | ATG | GAC | CGG | GCC | CAG | ATG | GAC |
| Sequenc found | TGC | CTG | TAT | GTG | ATG | GAC | AGA | GCA | CAA | ATG | GAC |

TABLE 3

```
1
GAGGAAGTCCCCGAGGCGCACAGAGCAAGCCCACGCGAGGGCACCTCTGGAGGGGAGCGCCTGCAGGACCTTGTAAAGTC
  81
AAAA MET SER GLU THR SER ARG THR ALA PHE GLY GLY ARG ARG ALA VAL PRO PRO ASN ASN
     ATG TCA GAA ACT TCC AGG ACC GCC TTT GGA GGC AGA AGA GCA GTT CCA CCC AAT AAC
  142
SER ASN ALA ALA GLU ASP ASP LEU PRO THR VAL GLU LEU GLN GLY VAL VAL PRO ARG GLY
TCT AAT GCA GCG GAA GAT GAC CTG CCC ACA GTG GAG CTT CAG GGC GTG GTG CCC CGG GGC
  202
VAL ASN LEU GLN GLU PHE LEU ASN VAL THR SER VAL HIS LEU PHE LYS GLU ARG TRP ASP
GTC AAC CTG CAA GAG TTT CTT AAT GTC ACG AGC GTT CAC CTG TTC AAG GAG AGA TGG GAC
  262
THR ASN LYS VAL ASP HIS HIS THR ASP LYS TYR GLU ASN ASN LYS LEU ILE VAL ARG ARG
ACT AAC AAG GTG GAC CAC CAC ACT GAC AAG TAT GAA AAC AAC AAG CTG ATT GTC CGC AGA
  322
```

TABLE 3-continued

```
GLY GLN SER PHE TYR VAL GLN ILE ASP LEU SER ARG PRO TYR ASP PRO ARG ARG ASP LEU
GGG CAG TCT TTC TAT GTG CAG ATT GAC CTC AGT CGT CCA TAT GAC CCC AGA AGG GAT CTC
382
PHE ARG VAL GLU TYR VAL ILE GLY ARG TYR PRO GLN GLU ASN LYS GLY THR TYR ILE PRO
TTC AGG GTG GAA TAC GTC ATT GGT CGC TAC CCA CAG GAG AAC AAG GGA ACC TAC ATC CCA
442
VAL PRO ILE VAL SER GLU LEU GLN SER GLY LYS TRP GLY ALA LYS ILE VAL MET ARG GLU
GTG CCT ATA GTC TCA GAG TTA CAA AGT GGA AAG TGG GGG GCC AAG ATT GTC ATG AGA GAG
502
ASP ARG SER VAL ARG LEU SER ILE GLN SER SER PRO LYS CYS ILE VAL GLY LYS PHE ARG
GAC AGG TCT GTG CGG CTG TCC ATC CAG TCT TCC CCC AAA TGT ATT GTG GGG AAA TTC CGC
562
MET TYR VAL ALA VAL TRP THR PRO TYR GLY VAL LEU ARG THR SER ARG ASN PRO GLU THR
ATG TAT GTT GCT GTC TGG ACT CCC TAT GGC GTA CTT CGA ACC AGT CGA AAC CCA GAA ACA
622
ASP THR TYR ILE LEU PHE ASN PRO TRP CYS GLU ASP ASP ALA VAL TYR LEU ASP ASN GLU
GAC ACG TAC ATT CTC TTC AAT CCT TGG TGT GAA GAT GAT GCT GTG TAT CTG GAC AAT GAG
682
LYS GLU ARG GLU GLU TYR VAL LEU ASN ASP ILE GLY VAL ILE PHE TYR GLY GLU VAL ASN
AAA GAA AGA GAA GAG TAT GTC CTG AAT GAC ATC GGG GTA ATT TTT TAT GGA GAG GTC AAT
742
ASP ILE LYS THR ARG SER TRP SER TYR GLY GLN PHE GLU ASP GLY ILE LEU ASP THR CYS
GAC ATC AAG ACC AGA AGC TGG AGC|TAT GGT CAG TTT GAA GAT GGC ATC CTG GAC ACT TGC
802
LEU TYR VAL MET ASP ARG ALA GLN MET ASP LEU SER GLY ARG GLY ASN PRO ILE LYS VAL
CTG TAT GTG ATG GAC AGA GCA CAA ATG GAC CTC TCT GGA AGA GGG AAT CCC ATC AAA GTC
                                      66 mer|
862
SER ARG VAL GLY SER ALA MET VAL ASN ALA LYS ASP ASP GLU GLY VAL LEU VAL GLY SER
AGC CGT GTG GGG TCT GCA ATG GTG AAT GCC AAA GAT GAC GAA GGT GTC CTC GTT GGA TCC
922
TRP ASP ASN ILE TYR ALA TYR GLY VAL PRO PRO SER ALA TRP THR GLY SER VAL ASP ILE
TGG GAC AAT ATC TAT GCC TAT GGC GTC CCC CCA TCG GCC TGG ACT GGA AGC GTT GAC ATT
982
LEU LEU GLU TYR ARG SER SER GLU ASN PRO VAL ARG TYR GLY GLN CYS TRP VAL PHE ALA
CTA TTG GAA TAC CGG AGC TCT GAG AAT CCA GTC CGG TAT GGC CAA TGC TGG GTT TTT GCT
1042
GLY VAL PHE ASN THR PHE LEU ARG CYS LEU GLY ILE PRO ALA ARG ILE VAL THR ASN TYR
GGT GTC TTT AAC ACA TTT TTA CGA TGC CTT GGA ATA CCA GCA AGA ATT GTT ACC AAT TAT
1102
PHE SER ALA HIS ASP ASN ASP ALA ASN LEU GLN MET ASP ILE PHE LEU GLU GLU ASP GLY
TTC TCT GCC CAT GAT AAT GAT GCC AAT TTG CAA ATG GAC ATC TTC CTG GAA GAA GAT GGG
1162
ASN VAL ASN SER LYS LEU THR LYS ASP SER VAL TRP ASN TYR HIS CYS TRP ASN GLU ALA
AAC GTG AAT TCC AAA CTC ACC AAG GAT TCA GTG TGG AAC TAC CAC TGC TGG AAT GAA GCA
1222
TRP MET THR ARG PRO ASP LEU PRO VAL GLY PHE GLY GLY TRP GLN ALA VAL ASP SER THR
TGG ATG ACA AGG CCT GAC CTT CCT GTT GGA TTT GGA GGC TGG CAA GCT GTG GAC AGC ACC
1282
PRO GLN GLU ASN SER ASP GLY MET TYR ARG CYS GLY PRO ALA SER VAL GLN ALA ILE LYS
CCC CAG GAA AAT AGC GAT GGC ATG TAT CGG TGT GGC CCC GCC TCG GTT CAA GCC ATC AAG
1342
HIS GLY HIS VAL CYS PHE GLN PHE ASP ALA PRO PHE VAL PHE ALA GLU VAL ASN SER ASP
CAC GGC CAT GTC TGC TTC CAA TTT GAT GCA CCT TTT GTT TTT GCA GAG GTC AAC AGC GAC
1402
LEU ILE TYR ILE THR ALA LYS LYS ASP GLY THR HIS VAL VAL GLU ASN VAL ASP ALA THR
CTC ATT TAC ATT ACA GCT AAG AAA GAT GGC ACT CAT GTG GTG GAA AAT GTG GAT GCC ACC
1462
HIS ILE GLY LYS LEU ILE VAL THR LYS GLN ILE GLY GLY ASP GLY MET MET ASP ILE THR
CAC ATT GGG AAA TTA ATT GTG ACC AAA CAA ATT GGA GGA GAT GGC|ATG ATG GAT ATT ACT
1522
ASP THR TYR LYS PHE GLN GLU GLY GLN GLU GLU GLU ARG LEU ALA LEU GLU THR ALA LEU
GAT ACT TAC AAA TTC CAA GAA GGT CAA GAA GAA GAG AGA TTG GCC CTA GAA ACT GCC CTG
20 mer|
1582
MET TYR GLY ALA LYS LYS PRO LEU ASN THR GLU GLY VAL MET LYS SER ARG SER ASN VAL
ATG TAC GGA GCT AAA AAG CCC CTC AAC ACA GAA GGT GTC ATG AAA TCA AGG TCC AAC GTT
1642
ASP MET ASP PHE GLU VAL GLU ASN ALA VAL LEU GLY LYS ASP PHE LYS LEU SER ILE THR
GAC ATG GAC TTT GAA GTG GAA AAT GCT GTG CTG GGA AAA GAC TTC AAG CTC TCC ATC ACC
1702
PHE ARG ASN ASN SER HIS ASN ARG TYR THR ILE THR ALA TYR LEU SER ALA ASN ILE THR
TTC CGG AAC AAC AGC CAC AAC CGT TAC ACC ATC ACA GCT TAT CTC TCA GCC AAC ATC ACC
1762
PHE TYR THR GLY VAL PRO LYS ALA GLU PHE LYS LYS GLU THR PHE ASP VAL THR LEU GLU
TTC TAC ACC GGG GTC CCG AAG GCA GAG TTC AAG AAG GAG ACG TTC GAC GTG ACG CTG GAG
1822
PRO LEU SER PHE LYS LYS GLU ALA VAL LEU ILE GLN ALA GLY GLU TYR MET GLY GLN LEU
CCC TTG TCC TTC AAG AAA GAG GCG GTG CTG ATC CAA GCC GGC GAG TAC ATG GGT CAG CTG
```

TABLE 3-continued

```
1882
LEU GLU GLN ALA SER LEU HIS PHE PHE VAL THR ALA ARG ILE ASN GLU THR ARG ASP VAL
CTG GAA CAA GCG TCC CTG CAC TTC TTT GTC ACA GCT CGC ATC AAT GAG ACC AGG GAT GTT
1942
LEU ALA LYS GLN LYS SER THR VAL LEU THR ILE PRO GLU ILE ILE ILE LYS VAL ARG GLY
CTG GCC AAG CAA AAG TCC ACC GTG CTA ACC ATC CCT GAG ATC ATC ATC AAG GTC CGT GGC
2002
THR GLN VAL VAL GLY SER ASP MET THR VAL THR VAL GLN PHE THR ASN PRO LEU LYS GLU
ACT CAG GTA GTT GGT TCT GAC ATG ACT GTG ACA GTT CAG TTT ACC AAT CCT TTA AAA GAA
2062
THR LEU ARG ASN VAL TRP VAL HIS LEU ASP GLY PRO GLY VAL THR ARG PRO MET LYS LYS
ACC CTG CGA AAT GTC TGG GTA CAC CTG GAT GGT CCT GGA GTA ACA AGA CCA ATG AAG AAG
2122
MET PHE ARG GLU ILE ARG PRO ASN SER THR VAL GLN TRP GLU GLU VAL CYS ARG PRO TRP
ATG TTC CGT GAA ATC CGG CCC AAC TCC ACC GTG CAG TGG GAA GAA GTG TGC CGG CCC TGG
2182
VAL SER GLY HIS ARG LYS LEU ILE ALA SER MET SER SER ASP SER LEU ARG HIS VAL TYR
GTC TCT GGG CAT CGG AAG CTG ATA GCC AGC ATG AGC AGT GAC TCC CTG AGA CAT GTG TAT
2242
GLY GLU LEU ASP VAL GLN ILE GLN ARG ARG PRO SER MET SSS ATGCACAGGAAGCTGAGATGAAC
GGC GAG CTG GAC GTG CAG ATT CAA AGA CGA CCT TCC ATG TGA
2307
CCTGGCATTTGGCCTCTTGTAGTCTTGGCTAAGGAAATTCTAACGCAAAAATAGCTCTTGCTTTGACTTAGGTGTGAAGA
2387
CCCAGACAGGACTGCAGAGGGCCCCAGAGTGGAGATCCCACATATTTCAAAAACATACTTTTCCAAACCCAGGCTATTCG
2467
GCAAGGAAGTTAGTTTTTAATCTCTCCACCTTCCAAAGAGTGCTAAGCATTAGCTTTAATTAAGCTCTCATAGCTCATAA
2547
GAGTAACAGTCATCATTTATCATCACAAATGGCTACATCTCCAAATATCAGTGGGCTCTCTTACCAGGGAGATTTGCTCA
2627
ATACCTGGCCTCATTTAAAACAAGACTTCAGATTCCCCACTCAGCCTTTTGGGAATAATAGCACATGATTTGGGCTCTAG
2707
AATTCCAGTCCCCTTTCTCGGGGTCAGGTTCTACCCTCCATGTGAGAATATTTTTCCCAGGACTAGAGCACAACATAATT
2787
TTTATTTTTGGCAAAGCCAGAAAAAGATCTTTCATTTTGCACCTGCAGCCAAGCAAATGCCTGCCAAATTTTAGATTTAC
2867
CTTGTTAGAAGAGGTGGCCCCATATTAACAAATTGCATTTGTGGGAAACTTAACCACCTACAAGGAGATAAGAAAGCAGG
2947
TGCAACACTCAAGTCTATTGAATAATGTAGTTTTGTGATGCATTTTATAGAATGTGTCACACTGTGGCCTGATCAGCAGG
3027
AGCCAATATCCCTTACTTTAACCCTTTCTGGGATGCAATACTAGGAAGTAAAGTGAAGAATTTATCTCTTTAGTTAGTGA
3107
TTATATTTCACCCATCTCTCAGGAATCATCTCCTTTGCAGAATGATGCAGGTTCAGGTCCCCTTTCAGAGATATAATAAG
3187
CCCAACAAGTTGAAGAAGCTGGCGGATCTAGTGACCAGATATATAGAAGGACTGCAGCCACTGATTCTCTCTTGTCCTTC
3267
ACATCACCATTTTGAGACCTCAGCTTGGCACTCAGGTGCTGAAGGGTAATATGGACTCAGCCTTGCAAATAGCCAGTGCT
3347
AGTTCTGACCCAACCACAGAGGATGCTGACATCATTTGTATTATGTTCCAAGGCTACTACAGAGAAGGCTGCCTGCTATG
3427
TATTTGCAAGGCTGATTTATGGTCAGAATTTCCCTCTGATATGTCTAGGGTGTGATTTAGGTCAGTAGACTGTGATTCTT
3507
AGCAAAAAATGAACAGTGATAAGTATACTGGGGGCAAAATCAGAATGGAATGCTCTGGTCTATATAACCACATTTCTGAG
3587
CCTTTGAGACTGTTCCTGAGCCTTCAGCACTAACCTATGAGGGTGAGCTGGTCCCCTCTATATATACATCATACTTAACT
3667
TTACTAAGTAATCTCACAGCATTTGCCAAGTCTCCCAATATCCAATTTTAAAATGAAATGCATTTTGCTAGACAGTTAAA
3747
CTGGCTTAACTTAGTATATTATTATTAATTACAATGTAATAGAAGCTTAAAATAAAGTTAAACTGATTATAAAAAAAAAA
3827
AAAAAAAAAAAAAAAAAAAAAAAAAAAAAAAAAAAAAAAAAAAAAAAAAAAAAAAAAAAAAAAAAAA
```

TABLE 4

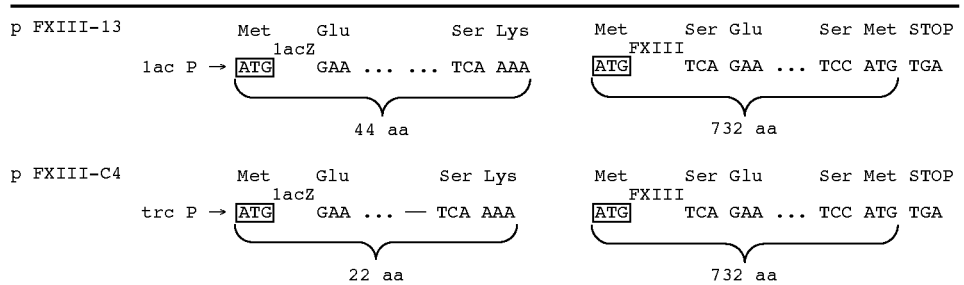

TABLE 4-continued

| pMB259 | | | | | | | | | | | |
|---|---|---|---|---|---|---|---|---|---|---|---|
| | | Met | Thr | | Asp | Pro | Asp | Pro | Arg | Gly | Ser M t STOP |
| | lacZ | | | | | | | 37 | 38 | 39 | |
| lac P → | ATG | ACC | ... | ... | GAT | GGG | GAT | CCC | CGG | GGC | ... TCC ATG TGA |
| | ⟵――――― 377 aa ―――――⟶ | | | | | ⟵――――― 696 aa ―――――⟶ | | | | | | aa = amino acids

Appendix
Example 1 from German Patent Application P 36 24 453.8
a) Construction of an expression vector for animal cells The plasmid pSV2dhfr (Lee et al., loc. cit.) was cut with HindIII and EcoRI, and the 2.65 kb vector fragment which has the SV40 early promotor was isolated. A 67 bp HindIII-EcoRI fragment from pUC12 STOP (Broker and Amann, Appl. Microbiol. Biotechnol. 23 (1986) 294–296) was ligated into the vector which had been pretreated in this way, which results in the plasmid pSV2 STOP. On the 67 bp fragment from pUC12 STOP there are translation stop codons in all three reading frames. pSV2 STOP was linearized with SacI, and the resulting 3' protruding end was removed using the 3'→5' exonuclease activity of DNA polymerase I. Then digestion with EcoRI was carried out. After ligation with an EcoRI-HpaI fragment 133 bp in size from pBB3 (B. Bourachot et al., EMBO J. 1 (1982) 895–900), which has the SV40 polyadenylation signal for early transcripts, it was possible to obtain the expression vector pSVA STOP1.

The polyadenylation site can also be isolated from the vector pIG6 (Bourachot et al., loc. cit.). It is possible in exactly the same way to isolate from the SV40 gene the 133 bp BamHI-HapI fragment, to fill in the BamHI cleavage site, and to attach an EcoRI linker.

pSVA STOP1 thus has, between the SV40 early promotor and the SV40 polyadenylation signal for early transcripts, a cloning polylinker with three unique restriction sites (HindIII-SalI-XbaI) and a sequence with translation stops in all three reading frames.

c) Construction of DHFR expression vectors for co-transfection

The starting point for the DHFR vectors used for the co-transfection was the plasmid pMTVdhfr (Lee et al., loc. cit.). pMTVdhfr was cut with BglII, and the protruding 5' ends of the DNA were filled in using DNA polymerase I (Klenow fragment). After digestion with EcoRI, a fragment 4.47 kb in size was isolated and ligated with a 133 bp EcoRI-HpaI fragment from pBB3 (Bourachot et al., loc. cit.). The new plasmid pMTVAdhfr has the mouse DHFR cDNA flanked by MMTV-LTR and the SV40 polyadenylation site for early transcripts.

pSVOAdhfr was obtained from pMTVAdhfr by deletion of a HindIII fragment which is 1450 bp in size and has the MMTV-LTR.

Neither pMTVAdhfr nor pSVOAdhfr have mRNA splice sites.

What is claimed is:

1. A method for producing factor XIIIa comprising operably inserting a DNA comprising the sequence set forth in FIG. 6, or naturally occurring alleles thereof, into a suitable vector, transforming an appropriate host cell with said vector, and expressing Factor XIIIa.

2. A method for producing a variant of a Factor XIIIa comprising operably inserting a DNA comprising a sequence from nucleotide position 82 to nucleotide position 2280 of FIG. 6, or degenerate variants thereof, into a suitable expression vector, transforming an appropriate host cell with said vector, and expressing said variant of a Factor XIIIa, wherein said variant of a Factor XIIIa has fibrin fusion catalysis activity.

3. A method for producing a variant of a Factor XIIIa comprising operably inserting a fragment of a DNA comprising the sequence set forth in FIG. 6, or naturally occurring alleles thereof, into a suitable expression vector, transforming an appropriate host cell with said vector, and expressing said variant of a Factor XIIIa, wherein said variant of a Factor XIIIa has fibrin fusion catalysis activity.

4. A method for producing a variant of a Factor XIIIa comprising operably inserting a DNA comprising a sequence from nucleotide position 199 to nucleotide position 2280 of FIG. 6, or degenerate variants thereof, into a suitable expression vector, transforming an appropriate host cell with said vector, and expressing said variant of a Factor XIIIa, wherein said variant of a Factor XIIIa has fibrin fusion catalysis activity.

5. The method according to claim 1, wherein the DNA comprises the sequence set forth in FIG. 6.

6. The method according to claim 3, wherein the DNA comprises the sequence set forth in FIG. 6.

7. The method according to claim 1, 2, 3 or 4, wherein the vector further comprises the strong ADHI promoter.

8. The method according to claim 1, 2, 3 or 4, wherein the host cell is an animal cell.

9. The method according to claim 8, wherein the animal cell is a CHO cell.

10. The method according to claim 1, 2, 3 or 4, wherein the host cell is an *Escherichia coli* cell.

11. The method according to claim 1, 2, 3 or 4, wherein the host cell is a yeast cell.

12. The method according to claim 11, wherein the yeast cell is a *Saccharomyces cerevisiae* cell.

13. The method according to claim 7, wherein the host cell is a yeast cell.

14. The method according to claim 13, wherein the yeast cell is a *Saccharomyces cerevisiae* cell.

15. The method according to claim 5 or 6, wherein the vector further comprises the strong ADHI promoter.

16. The method according to claim 5 or 6, wherein the host cell is an animal cell.

17. The method according to claim 16, wherein the animal cell is a CHO cell.

18. The method according to claim 5 or 6, wherein the host cell is an *Escherichia coli* cell.

19. The method according to claim 5 or 6, wherein the host cell is a yeast cell.

20. The method according to claim 19, wherein the yeast cell is a *Saccharomyces cerevisiae* cell.

21. The method according to claim 15, wherein the host cell is a yeast cell.

22. The method according to claim 21, wherein the yeast cell is a *Saccharomyces cerevisiae* cell.

23. An isolated DNA comprising the DNA sequence set forth in FIG. 6 or naturally occurring alleles thereof.

24. An isolated DNA comprising the DNA sequence from nucleotide position 82 to nucleotide position 2280 of FIG. 6 or degenerate variants thereof.

25. An isolated DNA comprising a fragment of the DNA sequence set forth in FIG. 6 or naturally occurring alleles thereof.

26. An isolated DNA comprising the DNA sequence from nucleotide position 199 to nucleotide position 2280 of FIG. 6 or degenerate variants thereof.

27. A vector comprising the isolated DNA according to claims 23, 24, 25, or 26.

28. A vector according to claim 27, further comprising the strong ADHI promoter.

29. A host cell comprising the vector according to claim 27.

30. The host cell according to claim 29, wherein the host cell is an animal cell.

31. The host cell according to claim 30, wherein the animal cell is a CHO cell.

32. The host cell according to claim 29, wherein the host cell is an *Escherichia coli* cell.

33. The host cell according to claim 29, wherein the host cell is a yeast cell.

34. The host cell according to claim 33, wherein the yeast cell is a *Saccharomyces cerevisiae* cell.

35. The host cell comprising the vector according to claim 28.

36. The host cell according to claim 35, wherein the host cell is a yeast cell.

37. The host cell according to claim 36, wherein the yeast cell is a *Saccharomyces cerevisiae* cell.

* * * * *